United States Patent
Bae et al.

(10) Patent No.: US 10,597,686 B2
(45) Date of Patent: Mar. 24, 2020

(54) POLYPEPTIDE HAVING THE ACTIVITY OF EXPORTING O-ACETYL-HOMOSERINE

(71) Applicant: CJ Cheiljedang Corporation, Seoul (KR)

(72) Inventors: Jee Yeon Bae, Gyeonggi-do (KR); Ji Hyun Shim, Seoul (KR); Hyun Ah Kim, Gyeonggi-do (KR); Juhee Seo, Gyeonggi-do (KR); Yong Uk Shin, Gyeonggi-do (KR); Jae Hee Lee, Seoul (KR); Sang Kyoum Kim, Gyeonggi-do (KR); So Young Kim, Gyeonggi-do (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/514,777

(22) Filed: Jul. 17, 2019

(65) Prior Publication Data
US 2019/0338322 A1    Nov. 7, 2019

Related U.S. Application Data

(62) Division of application No. 15/579,188, filed as application No. PCT/KR2016/005951 on Jun. 3, 2016, now Pat. No. 10,400,256.

(30) Foreign Application Priority Data

Jun. 4, 2015    (KR) ........................ 10-2015-0079358

(51) Int. Cl.
| | |
|---|---|
| C12P 13/06 | (2006.01) |
| C12P 13/12 | (2006.01) |
| C12N 15/70 | (2006.01) |
| C07K 14/245 | (2006.01) |

(52) U.S. Cl.
CPC ............ *C12P 13/06* (2013.01); *C07K 14/245* (2013.01); *C12N 15/70* (2013.01); *C12P 13/12* (2013.01)

(58) Field of Classification Search
None
See application file for complete search history.

(56) References Cited

U.S. PATENT DOCUMENTS

2009/0298135 A1   12/2009  Maier et al.

FOREIGN PATENT DOCUMENTS

| | | |
|---|---|---|
| EP | 2657250 A2 | 10/2013 |
| JP | 2011045360 | 3/2011 |
| JP | 2012213401 | 11/2012 |
| JP | 2013539987 | 10/2013 |
| KR | 10-0905381 B1 | 6/2009 |
| KR | 10-0951766 B1 | 4/2010 |
| KR | 10-1117012 B1 | 3/2012 |
| KR | 10-1250651 B1 | 4/2013 |
| KR | 10-1335841 B1 | 12/2013 |
| RU | 2175351 C2 | 10/2001 |
| WO | WO 2008-013432 A1 | 1/2008 |
| WO | WO 2008/142034 A2 | 11/2008 |
| WO | WO 2012-087039 A2 | 6/2012 |
| WO | WO 2014/145334 A1 | 9/2014 |

OTHER PUBLICATIONS

Accession A8AOZ3. Oct. 23, 2007, 1 page.
NCBI, NCBI Reference Sequence: WP_000457206.1, "MULTISPECIES: leucine efflux protein [Enterobacteriaceae]," Jne page, Oct. 20, 2014.
Kutukova et al, "The yeas {leuE} gene of *Escherichia coli* encodes an exporter of leucine, and the Lrp protein egulates its expression of leucine, and the Lrp protein regulates its expression," FEBS Letters, vol. 579, pp. 4629-463' 2005).
UniProtKb-P76249 (LEUE_ECOLI), dated Jul. 15, 1998, 1 page, retrieved online at www.uniprot.org/uniprot/P76249 on Dec. 6, 2018.
Leucine export protein LeuE{ECO:0000313:EMBL:KDM91107.1}, UniProt Accession No. A0A066RTU4, dated Sep. 3, 2014, 1 page.
Leucine export protein LeuE [*Providencia stuartii* MRSN2154], GenBank Accession No. AFH92508.1, Jan. 31, 2014, 1 page.
Environmental stress related sequence, SEQ ID 8934, GeneSeq Accession No. AWF72241, dated Jul. 9, 2009, 2 pages.
GenBank, Dec. 16, 2014, Accession No. NP_416312, 3 pages.

*Primary Examiner* — Christian L Fronda
(74) *Attorney, Agent, or Firm* — Cooley LLP

(57) ABSTRACT

The present disclosure relates to a protein having the activity of exporting O-acetylhomoserine and a novel modified protein thereof, a microorganism capable of producing O-acetylhomoserine with enhanced expression of the protein, and a method for producing O-acetylhomoserine using the microorganism.

13 Claims, No Drawings
Specification includes a Sequence Listing.

SEQUENCE LISTING

```
<160> NUMBER OF SEQ ID NOS: 146

<210> SEQ ID NO 1
<211> LENGTH: 212
<212> TYPE: PRT
<213> ORGANISM: Escherichia coli

<400> SEQUENCE: 1

Val Phe Ala Glu Tyr Gly Val Leu Asn Tyr Trp Thr Tyr Leu Val Gly
1               5                   10                  15

Ala Ile Phe Ile Val Leu Val Pro Gly Pro Asn Thr Leu Phe Val Leu
            20                  25                  30

Lys Asn Ser Val Ser Ser Gly Met Lys Gly Gly Tyr Leu Ala Ala Cys
        35                  40                  45

Gly Val Phe Ile Gly Asp Ala Val Leu Met Phe Leu Ala Trp Ala Gly
    50                  55                  60

Val Ala Thr Leu Ile Lys Thr Thr Pro Ile Leu Phe Asn Ile Val Arg
65                  70                  75                  80

Tyr Leu Gly Ala Phe Tyr Leu Leu Tyr Leu Gly Ser Lys Ile Leu Tyr
                85                  90                  95

Ala Thr Leu Lys Gly Lys Asn Ser Glu Ala Lys Ser Asp Glu Pro Gln
            100                 105                 110

Tyr Gly Ala Ile Phe Lys Arg Ala Leu Ile Leu Ser Leu Thr Asn Pro
        115                 120                 125

Lys Ala Ile Leu Phe Tyr Val Ser Phe Phe Val Gln Phe Ile Asp Val
    130                 135                 140

Asn Ala Pro His Thr Gly Ile Ser Phe Phe Ile Leu Ala Ala Thr Leu
145                 150                 155                 160

Glu Leu Val Ser Phe Cys Tyr Leu Ser Phe Leu Ile Ile Ser Gly Ala
                165                 170                 175

Phe Val Thr Gln Tyr Ile Arg Thr Lys Lys Lys Leu Ala Lys Val Gly
            180                 185                 190

Asn Ser Leu Ile Gly Leu Met Phe Val Gly Phe Ala Ala Arg Leu Ala
        195                 200                 205

Thr Leu Gln Ser
    210

<210> SEQ ID NO 2
<211> LENGTH: 212
<212> TYPE: PRT
<213> ORGANISM: Artificial Sequence
<220> FEATURE:
<223> OTHER INFORMATION: Made in lab - substituted LeuE variant
```

<400> SEQUENCE: 2

Met Phe Ala Glu Tyr Gly Val Leu Asn Tyr Trp Thr Tyr Leu Val Gly
1               5                   10                  15

Ala Ile Phe Ile Val Leu Val Pro Gly Pro Asn Thr Leu Phe Val Leu
            20                  25                  30

Lys Asn Ser Val Ser Ser Gly Met Lys Gly Gly Tyr Leu Ala Ala Cys
        35                  40                  45

Gly Val Phe Ile Gly Asp Ala Val Leu Met Phe Leu Ala Trp Ala Gly
    50                  55                  60

Val Ala Thr Leu Ile Lys Thr Thr Pro Ile Leu Phe Asn Ile Val Arg
65                  70                  75                  80

Tyr Leu Gly Ala Phe Tyr Leu Leu Tyr Leu Gly Ser Lys Ile Leu Tyr
                85                  90                  95

Ala Thr Leu Lys Gly Lys Asn Ser Glu Ala Lys Ser Asp Glu Pro Gln
            100                 105                 110

Tyr Gly Ala Ile Phe Lys Arg Ala Leu Ile Leu Ser Leu Thr Asn Pro
        115                 120                 125

Lys Ala Ile Leu Phe Tyr Val Ser Phe Phe Val Gln Phe Ile Asp Val
130                 135                 140

Asn Ala Pro His Thr Gly Ile Ser Phe Phe Ile Leu Ala Ala Thr Leu
145                 150                 155                 160

Glu Leu Val Ser Phe Cys Tyr Leu Ser Phe Leu Ile Ile Ser Gly Ala
                165                 170                 175

Phe Val Thr Gln Tyr Ile Arg Thr Lys Lys Lys Leu Ala Lys Val Gly
            180                 185                 190

Asn Ser Leu Ile Gly Leu Met Phe Val Gly Phe Ala Ala Arg Leu Ala
        195                 200                 205

Thr Leu Gln Ser
    210

<210> SEQ ID NO 3
<211> LENGTH: 639
<212> TYPE: DNA
<213> ORGANISM: Escherichia coli

<400> SEQUENCE: 3
gtgttcgctg aatacggggt tctgaattac tggacctatc tggttggggc catttttatt      60
gtgttggtgc cagggccaaa taccctgttt gtactcaaaa atagcgtcag tagcggtatg     120
aaaggcggtt atcttgcggc ctgcggtgta tttattggcg atgcggtatt gatgtttctg     180
gcatgggctg gagtggcgac attaattaag accaccccga tattattcaa cattgtacgt     240
tatcttggtg cgttttattt gctctatctg gggagtaaaa ttctttacgc gacccctgaag    300 ggtaaaaata gcgaggccaa atccgatgag ccccaatacg gtgctatttt taaacgcgcg     360 ttaatttttga gcctgactaa tccgaaagcc attttgttct atgtgtcgtt tttcgtacag    420
tttatcgatg ttaatgcccc acatacggga atttcattct ttattctggc ggcgacgctg    480
gaactggtga gtttctgcta tttgagcttc ctgattatat ctggtgcttt tgtcacgcag    540
tacatacgta ccaaaaagaa actggctaaa gttgcaact cactgattgg tttgatgttc      600
gtgggtttcg ctgcccgact ggcgacgctg caatcctga                            639

<210> SEQ ID NO 4
<211> LENGTH: 639
<212> TYPE: DNA

```
<213> ORGANISM: Artificial sequence
<220> FEATURE:
<223> OTHER INFORMATION: Made in lab - substituted LeuE variant

<400> SEQUENCE: 4
atgttcgctg aatacggggt tctgaattac tggacctatc tggttggggc catttttatt      60
gtgttggtgc cagggccaaa taccctgttt gtactcaaaa atagcgtcag tagcggtatg     120
aaaggcggtt atcttgcggc ctgcggtgta tttattggcg atgcggtatt gatgtttctg     180
gcatgggctg gagtggcgac attaattaag accaccccga tattattcaa cattgtacgt     240
tatcttggtg cgtttttattt gctctatctg gggagtaaaa ttctttacgc gaccctgaag     300
ggtaaaaata gcgaggccaa atccgatgag ccccaatacg gtgctatttt taaacgcgcg     360
ttaattttga gcctgactaa tccgaaagcc attttgttct atgtgtcgtt tttcgtacag     420
tttatcgatg ttaatgcccc acatacggga atttcattct ttattctggc ggcgacgctg     480
gaactggtga gtttctgcta tttgagcttc ctgattatat ctggtgcttt tgtcacgcag     540
tacatacgta ccaaaaagaa actggctaaa gttggcaact cactgattgg tttgatgttc     600
gtgggtttcg ctgcccgact ggcgacgctg caatcctga                              639

<210> SEQ ID NO 5
<211> LENGTH: 386
<212> TYPE: PRT
<213> ORGANISM: Escherichia coli

<400> SEQUENCE: 5

Met Thr Arg Lys Gln Ala Thr Ile Ala Val Arg Ser Gly Leu Asn Asp
1               5                   10                  15

Asp Glu Gln Tyr Gly Cys Val Val Pro Ile His Leu Ser Ser Thr
            20                  25                  30

Tyr Asn Phe Thr Gly Phe Asn Glu Pro Arg Ala His Asp Tyr Ser Arg
        35                  40                  45

Arg Gly Asn Pro Thr Arg Asp Val Val Gln Arg Ala Leu Ala Glu Leu
    50                  55                  60

Glu Gly Gly Ala Gly Ala Val Leu Thr Asn Thr Gly Met Ser Ala Ile
65                  70                  75                  80

His Leu Val Thr Thr Val Phe Leu Lys Pro Gly Asp Leu Leu Val Ala
                85                  90                  95

Pro His Asp Cys Tyr Gly Gly Ser Tyr Arg Leu Phe Asp Ser Leu Ala
            100                 105                 110

Lys Arg Gly Cys Tyr Arg Val Leu Phe Val Asp Gln Gly Asp Glu Gln
        115                 120                 125

Ala Leu Arg Ala Ala Leu Ala Glu Lys Pro Lys Leu Val Leu Val Glu
    130                 135                 140

Ser Pro Ser Asn Pro Leu Leu Arg Val Val Asp Ile Ala Lys Ile Cys
145                 150                 155                 160

His Leu Ala Arg Glu Val Gly Ala Val Ser Val Val Asp Asn Thr Phe
                165                 170                 175

Leu Ser Pro Ala Leu Gln Asn Pro Leu Ala Leu Gly Ala Asp Leu Val
            180                 185                 190

Leu His Ser Cys Thr Lys Tyr Leu Asn Gly His Ser Asp Val Val Ala
        195                 200                 205

Gly Val Val Ile Ala Lys Asp Pro Asp Val Val Thr Glu Leu Ala Trp
    210                 215                 220

Trp Ala Asn Asn Ile Gly Val Thr Gly Gly Ala Phe Asp Ser Tyr Leu
```

```
                    225                 230                 235                 240
Leu Leu Arg Gly Leu Arg Thr Leu Val Pro Arg Met Glu Leu Ala Gln
                245                 250                 255

Arg Asn Ala Gln Ala Ile Val Lys Tyr Leu Gln Thr Gln Pro Leu Val
                260                 265                 270

Lys Lys Leu Tyr His Pro Ser Leu Pro Glu Asn Gln Gly His Glu Ile
            275                 280                 285

Ala Ala Arg Gln Gln Lys Gly Phe Gly Ala Met Leu Ser Phe Glu Leu
        290                 295                 300

Asp Gly Asp Glu Gln Thr Leu Arg Arg Phe Leu Gly Leu Ser Leu
305                 310                 315                 320

Phe Thr Leu Ala Glu Ser Leu Gly Gly Val Glu Ser Leu Ile Ser His
                325                 330                 335

Ala Ala Thr Met Thr His Ala Gly Met Ala Pro Glu Ala Arg Ala Ala
                340                 345                 350

Ala Gly Ile Ser Glu Thr Leu Leu Arg Ile Ser Thr Gly Ile Glu Asp
            355                 360                 365

Gly Glu Asp Leu Ile Ala Asp Leu Glu Asn Gly Phe Arg Ala Ala Asn
        370                 375                 380

Lys Gly
385

<210> SEQ ID NO 6
<211> LENGTH: 1161
<212> TYPE: DNA
<213> ORGANISM: Escherichia coli

<400> SEQUENCE: 6
atgacgcgta acaggccac catcgcagtg cgtagcgggt taaatgacga cgaacagtat      60
ggttgcgttg tcccaccgat ccatctttcc agcacctata actttaccgg atttaatgaa    120
ccgcgcgcgc atgattactc gcgtcgcggc aacccaacgc gcgatgtggt tcagcgtgcg    180
ctggcagaac tggaaggtgg tgctggtgca gtacttacta ataccggcat gtccgcgatt    240
cacctggtaa cgaccgtctt tttgaaacct ggcgatctgc tggttgcgcc gcacgactgc    300
tacggcggta gctatcgcct gttcgacagt ctggcgaaac gcggttgcta tcgcgtgttg    360
tttgttgatc aaggcgatga acaggcatta cgggcagcgc tggcagaaaa acccaaactg    420
gtactggtag aaagcccaag taatccattg ttacgcgtcg tggatattgc gaaaatctgc    480
catctggcaa gggaagtcgg ggcggtgagc gtggtggata caccttctt aagcccggca    540 ttacaaaatc cgctggcatt aggtgccgat ctggtgttgc attcatgcac gaaatatctg    600
aacggtcact cagacgtagt ggccggcgtg gtgattgcta agacccgga cgttgtcact    660 gaactggcct ggtgggcaaa caatattggc gtgacgggcg gcgcgtttga cagctatctg    720
ctgctacgtg ggttgcgaac gctggtgccg cgtatggagc tggcgcagcg caacgcgcag    780
gcgattgtga atacctgca aacccagccg ttggtgaaaa aactgtatca cccgtcgttg    840
ccggaaaatc aggggcatga aattgccgcg cgccagcaaa aaggctttgg cgcaatgttg    900
agttttgaac tggatggcga tgagcagacg ctgcgtcgtt tcctgggcgg gctgtcgttg    960
tttacgctgg cggaatcatt agggggagtg gaaagtttaa tctctcacgc cgcaaccatg   1020
acacatgcag gcatggcacc agaagcgcgt gctgccgccg ggatctccga gacgctgctg   1080
cgtatctcca ccggtattga agatggcgaa gatttaattg ccgacctgga aaatggcttc   1140
cgggctgcaa acaagggta a                                             1161
```

<210> SEQ ID NO 7
<211> LENGTH: 310
<212> TYPE: PRT
<213> ORGANISM: Escherichia coli

<400> SEQUENCE: 7

```
Met Val Lys Val Tyr Ala Pro Ala Ser Ser Ala Asn Met Ser Val Gly
1               5                   10                  15

Phe Asp Val Leu Gly Ala Ala Val Thr Pro Val Asp Gly Ala Leu Leu
            20                  25                  30

Gly Asp Val Val Thr Val Glu Ala Ala Glu Thr Phe Ser Leu Asn Asn
        35                  40                  45

Leu Gly Arg Phe Ala Asp Lys Leu Pro Ser Glu Pro Arg Glu Asn Ile
    50                  55                  60

Val Tyr Gln Cys Trp Glu Arg Phe Cys Gln Glu Leu Gly Lys Gln Ile
65                  70                  75                  80

Pro Val Ala Met Thr Leu Glu Lys Asn Met Pro Ile Gly Ser Gly Leu
                85                  90                  95

Gly Ser Ser Ala Cys Ser Val Val Ala Ala Leu Met Ala Met Asn Glu
            100                 105                 110

His Cys Gly Lys Pro Leu Asn Asp Thr Arg Leu Leu Ala Leu Met Gly
        115                 120                 125

Glu Leu Glu Gly Arg Ile Ser Gly Ser Ile His Tyr Asp Asn Val Ala
    130                 135                 140

Pro Cys Phe Leu Gly Gly Met Gln Leu Met Ile Glu Glu Asn Asp Ile
145                 150                 155                 160

Ile Ser Gln Gln Val Pro Gly Phe Asp Glu Trp Leu Trp Val Leu Ala
                165                 170                 175

Tyr Pro Gly Ile Lys Val Ser Thr Ala Glu Ala Arg Ala Ile Leu Pro
            180                 185                 190

Ala Gln Tyr Arg Arg Gln Asp Cys Ile Ala His Gly Arg His Leu Ala
        195                 200                 205

Gly Phe Ile His Ala Cys Tyr Ser Arg Gln Pro Glu Leu Ala Ala Lys
    210                 215                 220

Leu Met Lys Asp Val Ile Ala Glu Pro Tyr Arg Glu Arg Leu Leu Pro
225                 230                 235                 240

Gly Phe Arg Gln Ala Arg Gln Ala Val Ala Glu Ile Gly Ala Val Ala
                245                 250                 255

Ser Gly Ile Ser Gly Ser Gly Pro Thr Leu Phe Ala Leu Cys Asp Lys
            260                 265                 270

Pro Glu Thr Ala Gln Arg Val Ala Asp Trp Leu Gly Lys Asn Tyr Leu
        275                 280                 285

Gln Asn Gln Glu Gly Phe Val His Ile Cys Arg Leu Asp Thr Ala Gly
    290                 295                 300

Ala Arg Val Leu Glu Asn
305                 310
```

<210> SEQ ID NO 8
<211> LENGTH: 933
<212> TYPE: DNA
<213> ORGANISM: Escherichia coli

<400> SEQUENCE: 8
atggttaaag tttatgcccc ggcttccagt gccaatatga gcgtcgggtt tgatgtgctc    60

```
ggggcggcgg tgacacctgt tgatggtgca ttgctcggag atgtagtcac ggttgaggcg      120
gcagagacat tcagtctcaa caacctcgga cgctttgccg ataagctgcc gtcagaacca      180
cgggaaaata tcgttttatca gtgctgggag cgttttttgcc aggaactggg taagcaaatt    240
```

```
ggggcggcgg tgacacctgt tgatggtgca ttgctcggag atgtagtcac ggttgaggcg      120
gcagagacat tcagtctcaa caacctcgga cgctttgccg ataagctgcc gtcagaacca      180
cgggaaaata tcgtttatca gtgctgggag cgttttgcc aggaactggg taagcaaatt       240
ccagtggcga tgaccctgga aaagaatatg ccgatcggtt cgggcttagg ctccagtgcc      300
tgttcggtgg tcgcggcgct gatggcgatg aatgaacact gcggcaagcc gcttaatgac      360
actcgtttgc tggctttgat gggcgagctg gaaggccgta tctccggcag cattcattac      420
gacaacgtgg caccgtgttt tctcggtggt atgcagttga tgatcgaaga aaacgacatc      480
atcagccagc aagtgccagg gtttgatgag tggctgtggg tgctggcgta tccggggatt      540
aaagtctcga cggcagaagc cagggctatt ttaccggcgc agtatcgccg ccaggattgc      600
attgcgcacg gcgacatctg gcaggcttc attcacgcct gctattcccg tcagcctgag       660
cttgccgcga agctgatgaa agatgttatc gctgaaccct accgtgaacg gttactgcca      720
ggcttccggc aggcgcggca ggcggtcgcg gaaatcggcg cggtagcgag cggtatctcc      780
ggctccggcc cgaccttgtt cgctctgtgt gacaagccga aaccgccca gcgcgttgcc      840 gactggttgg gtaagaacta cctgcaaaat caggaaggtt ttgttcatat tgccggctg       900 gatacggcgg gcgcacgagt actggaaaac taa                                   933
```

<210> SEQ ID NO 9
<211> LENGTH: 309
<212> TYPE: PRT
<213> ORGANISM: Artificial Sequence
<220> FEATURE:
<223> OTHER INFORMATION: Made in Lab - substituted homoserine O-acetyl transferase

<400> SEQUENCE: 9

```
Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Glu His
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205
```

Glu Ile Leu Ala Glu Thr Glu Gly Asp Ala Tyr Leu Phe Ala Ser
            210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
            290                 295                 300

Asn Pro Thr Leu Asp
305

<210> SEQ ID NO 10
<211> LENGTH: 930
<212> TYPE: DNA
<213> ORGANISM: Artificial Sequence
<220> FEATURE:
<223> OTHER INFORMATION: Made in Lab - substituted homoserine O-acetyl
      transferase

<400> SEQUENCE: 10
atgccgattc gtgtgccgga cgagctaccc gccgtcaatt tcttgcgtga agaaaacgtc      60
tttgtgatga caacttctcg tgcgtctggt caggaaattc gtccacttaa ggttctgatc     120
cttaacctga tgccgaagaa gattgaaact gaaaatcagt ttctgcgcct gctttcaaac     180
tcacctttgc aggtcgatat tcagctgttg cgcatcgatt ccgtgaatc gcgcaacacg      240 cccgcagagc atctgaacaa cttctactgt aactttgaag atattcagga tcagaacttt     300
gacggtttga ttgtaactgg tgcgccgctg aacatgtgg agtttaatga tgtcgcttac      360
tggccgcaga tcaaacaggt gctggagtgg tcgaaagatc acgtcacctc gacgctgttt     420
gtctgctggg cggtacaggc cgcgctcaat atcctctacg gcattcctaa gcaaactcgc     480
accgaaaaac tctctggcgt ttacgagcat catattctcc atcctcatgc gcttctgacg     540
cgtggctttg atgattcatt cctggcaccg cattcgcgct atgctgactt ccggcagcg      600 ttgattcgtg attacaccga tctggaaatt ctggcagaga cggaagaagg ggatgcatat     660
ctgtttgcca gtaaagataa gcgcattgcc tttgtgacgg gccatccga atatgatgcg      720 caaacgctgg cgcaggaatt tttccgcgat gtggaagccg actagaccc ggatgtaccg      780 tataactatt tcccgcacaa tgatccgcaa aatacaccgc gagcgagctg gcgtagtcac     840
ggtaatttac tgtttaccaa ctggctcaac tattacgtct accagatcac gccatacgat     900
ctacggcaca tgaatccaac gctggattaa                                      930

<210> SEQ ID NO 11
<211> LENGTH: 27
<212> TYPE: DNA
<213> ORGANISM: Artificial Sequence
<220> FEATURE:
<223> OTHER INFORMATION: primer

<400> SEQUENCE: 11
cccgggtttt cactggagca tgcctga                                          27

<210> SEQ ID NO 12

```
<211> LENGTH: 27
<212> TYPE: DNA
<213> ORGANISM: Artificial Sequence
<220> FEATURE:
<223> OTHER INFORMATION: primer

<400> SEQUENCE: 12
cccggggcgc tgaaaacggt ttattcc                                    27

<210> SEQ ID NO 13
<211> LENGTH: 36
<212> TYPE: DNA
<213> ORGANISM: Artificial Sequence
<220> FEATURE:
<223> OTHER INFORMATION: primer

<400> SEQUENCE: 13
gctactgacg ctattcgcga gtacaaacag ggtatt                          36

<210> SEQ ID NO 14
<211> LENGTH: 36
<212> TYPE: DNA
<213> ORGANISM: Artificial Sequence
<220> FEATURE:
<223> OTHER INFORMATION: primer

<400> SEQUENCE: 14
cttcagggtc gcgtacacaa ttttactccc cagata                          36

<210> SEQ ID NO 15
<211> LENGTH: 26
<212> TYPE: DNA
<213> ORGANISM: Artificial Sequence
<220> FEATURE:
<223> OTHER INFORMATION: primer

<400> SEQUENCE: 15
cccgggaact caaattccct gataat                                     26

<210> SEQ ID NO 16
<211> LENGTH: 38
<212> TYPE: DNA
<213> ORGANISM: Artificial Sequence
<220> FEATURE:
<223> OTHER INFORMATION: primer

<400> SEQUENCE: 16
agacagttac accgtttaaa gtaccctgct ctatttaa                        38

<210> SEQ ID NO 17
<211> LENGTH: 38
<212> TYPE: DNA
<213> ORGANISM: Artificial Sequence
<220> FEATURE:
<223> OTHER INFORMATION: primer

<400> SEQUENCE: 17
ttaaatagag cagggtactt taaacggtgt aactgtct                        38

<210> SEQ ID NO 18
<211> LENGTH: 26
<212> TYPE: DNA
<213> ORGANISM: Artificial Sequence
<220> FEATURE:
<223> OTHER INFORMATION: primer

<400> SEQUENCE: 18
```
cccgggcggc tcagcagag gccgtc                                        26

<210> SEQ ID NO 19
<211> LENGTH: 29
<212> TYPE: DNA
<213> ORGANISM: Artificial Sequence
<220> FEATURE:
<223> OTHER INFORMATION: primer

<400> SEQUENCE: 19
aattgatatc atgccgattc gtgtgccgg                                    29

<210> SEQ ID NO 20
<211> LENGTH: 27
<212> TYPE: DNA
<213> ORGANISM: Artificial Sequence
<220> FEATURE:
<223> OTHER INFORMATION: primer

<400> SEQUENCE: 20
aattaagcct gctgaggtac gtttcgg                                      27

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
cagcaggtga ataaatttta ttc                                          23

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
cgcgaatgga agctgtttcc                                              20

<210> SEQ ID NO 23
<211> LENGTH: 42
<212> TYPE: DNA
<213> ORGANISM: Artificial Sequence
<220> FEATURE:
<223> OTHER INFORMATION: primer

<400> SEQUENCE: 23
tttccgaaac gtacctcagc aggtgtaggc tggagctgct tc                     42

<210> SEQ ID NO 24
<211> LENGTH: 43
<212> TYPE: DNA
<213> ORGANISM: Artificial Sequence
<220> FEATURE:
<223> OTHER INFORMATION: primer

<400> SEQUENCE: 24
gaataaaatt tattcacctg ctgcatatga atatcctcct tag                    43

<210> SEQ ID NO 25
<211> LENGTH: 36
<212> TYPE: DNA

```
<213> ORGANISM: Artificial Sequence
<220> FEATURE:
<223> OTHER INFORMATION: primer

<400> SEQUENCE: 25
gggccaaata ccctggcggt actcaaaaat agcgtc                              36

<210> SEQ ID NO 26
<211> LENGTH: 36
<212> TYPE: DNA
<213> ORGANISM: Artificial Sequence
<220> FEATURE:
<223> OTHER INFORMATION: primer

<400> SEQUENCE: 26
gacgctattt ttgagtaccg ccagggtatt tggccc                              36

<210> SEQ ID NO 27
<211> LENGTH: 36
<212> TYPE: DNA
<213> ORGANISM: Artificial Sequence
<220> FEATURE:
<223> OTHER INFORMATION: primer

<400> SEQUENCE: 27
aaagccattt tgttctctgt gtcgttttc gtacag                               36

<210> SEQ ID NO 28
<211> LENGTH: 36
<212> TYPE: DNA
<213> ORGANISM: Artificial Sequence
<220> FEATURE:
<223> OTHER INFORMATION: primer

<400> SEQUENCE: 28
ctgtacgaaa aacgacacag agaacaaaat ggcttt                              36

<210> SEQ ID NO 29
<211> LENGTH: 27
<212> TYPE: DNA
<213> ORGANISM: Artificial Sequence
<220> FEATURE:
<223> OTHER INFORMATION: primer

<400> SEQUENCE: 29 ggtaccttt cactggagca tgcctga                                         27

<210> SEQ ID NO 30
<211> LENGTH: 27
<212> TYPE: DNA
<213> ORGANISM: Artificial Sequence
<220> FEATURE:
<223> OTHER INFORMATION: primer

<400> SEQUENCE: 30
ggtaccgcgc tgaaaacggt ttattcc                                        27

<210> SEQ ID NO 31
<211> LENGTH: 36
<212> TYPE: DNA
<213> ORGANISM: Artificial Sequence
<220> FEATURE:
<223> OTHER INFORMATION: primer

<400> SEQUENCE: 31
tatctgggga gtaaaatttt ttacgcgacc ctgaag                              36
```

```
<210> SEQ ID NO 32
<211> LENGTH: 36
<212> TYPE: DNA
<213> ORGANISM: Artificial Sequence
<220> FEATURE:
<223> OTHER INFORMATION: primer

<400> SEQUENCE: 32
cttcagggtc gcgtaaaaaa ttttactccc cagata                          36

<210> SEQ ID NO 33
<211> LENGTH: 36
<212> TYPE: DNA
<213> ORGANISM: Artificial Sequence
<220> FEATURE:
<223> OTHER INFORMATION: primer

<400> SEQUENCE: 33
tatctgggga gtaaaattgc gtacgcgacc ctgaag                          36

<210> SEQ ID NO 34
<211> LENGTH: 36
<212> TYPE: DNA
<213> ORGANISM: Artificial Sequence
<220> FEATURE:
<223> OTHER INFORMATION: primer

<400> SEQUENCE: 34
cttcagggtc gcgtacgcaa ttttactccc cagata                          36

<210> SEQ ID NO 35
<211> LENGTH: 36
<212> TYPE: DNA
<213> ORGANISM: Artificial Sequence
<220> FEATURE:
<223> OTHER INFORMATION: primer

<400> SEQUENCE: 35
tatctgggga gtaaaattgg ctacgcgacc ctgaag                          36

<210> SEQ ID NO 36
<211> LENGTH: 36
<212> TYPE: DNA
<213> ORGANISM: Artificial Sequence
<220> FEATURE:
<223> OTHER INFORMATION: primer

<400> SEQUENCE: 36
cttcagggtc gcgtagccaa ttttactccc cagata                          36

<210> SEQ ID NO 37
<211> LENGTH: 36
<212> TYPE: DNA
<213> ORGANISM: Artificial Sequence
<220> FEATURE:
<223> OTHER INFORMATION: primer

<400> SEQUENCE: 37
tatctgggga gtaaaattac ctacgcgacc ctgaag                          36

<210> SEQ ID NO 38
<211> LENGTH: 36
<212> TYPE: DNA
<213> ORGANISM: Artificial Sequence
<220> FEATURE:
```

```
<223> OTHER INFORMATION: primer

<400> SEQUENCE: 38
cttcagggtc gcgtaggtaa ttttactccc cagata                              36

<210> SEQ ID NO 39
<211> LENGTH: 36
<212> TYPE: DNA
<213> ORGANISM: Artificial Sequence
<220> FEATURE:
<223> OTHER INFORMATION: primer

<400> SEQUENCE: 39
tatctgggga gtaaaattaa ctacgcgacc ctgaag                              36

<210> SEQ ID NO 40
<211> LENGTH: 36
<212> TYPE: DNA
<213> ORGANISM: Artificial Sequence
<220> FEATURE:
<223> OTHER INFORMATION: primer

<400> SEQUENCE: 40
cttcagggtc gcgtagttaa ttttactccc cagata                              36

<210> SEQ ID NO 41
<211> LENGTH: 36
<212> TYPE: DNA
<213> ORGANISM: Artificial Sequence
<220> FEATURE:
<223> OTHER INFORMATION: primer

<400> SEQUENCE: 41
tatctgggga gtaaaattga ttacgcgacc ctgaag                              36

<210> SEQ ID NO 42
<211> LENGTH: 36
<212> TYPE: DNA
<213> ORGANISM: Artificial Sequence
<220> FEATURE:
<223> OTHER INFORMATION: primer

<400> SEQUENCE: 42
cttcagggtc gcgtaatcaa ttttactccc cagata                              36

<210> SEQ ID NO 43
<211> LENGTH: 36
<212> TYPE: DNA
<213> ORGANISM: Artificial Sequence
<220> FEATURE:
<223> OTHER INFORMATION: primer

<400> SEQUENCE: 43
tatctgggga gtaaaattca ttacgcgacc ctgaag                              36

<210> SEQ ID NO 44
<211> LENGTH: 36
<212> TYPE: DNA
<213> ORGANISM: Artificial Sequence
<220> FEATURE:
<223> OTHER INFORMATION: primer

<400> SEQUENCE: 44
cttcagggtc gcgtaatgaa ttttactccc cagata                              36
```

-continued

<210> SEQ ID NO 45
<211> LENGTH: 36
<212> TYPE: DNA
<213> ORGANISM: Artificial Sequence
<220> FEATURE:
<223> OTHER INFORMATION: primer

<400> SEQUENCE: 45
tatctgggga gtaaaattat ttacgcgacc ctgaag                36

<210> SEQ ID NO 46
<211> LENGTH: 36
<212> TYPE: DNA
<213> ORGANISM: Artificial Sequence
<220> FEATURE:
<223> OTHER INFORMATION: primer

<400> SEQUENCE: 46
cttcagggtc gcgtaaataa ttttactccc cagata                36

<210> SEQ ID NO 47
<211> LENGTH: 36
<212> TYPE: DNA
<213> ORGANISM: Artificial Sequence
<220> FEATURE:
<223> OTHER INFORMATION: primer

<400> SEQUENCE: 47
tatctgggga gtaaaatttc ttacgcgacc ctgaag                36

<210> SEQ ID NO 48
<211> LENGTH: 36
<212> TYPE: DNA
<213> ORGANISM: Artificial Sequence
<220> FEATURE:
<223> OTHER INFORMATION: primer

<400> SEQUENCE: 48
cttcagggtc gcgtaagaaa ttttactccc cagata                36

<210> SEQ ID NO 49
<211> LENGTH: 36
<212> TYPE: DNA
<213> ORGANISM: Artificial Sequence
<220> FEATURE:
<223> OTHER INFORMATION: primer

<400> SEQUENCE: 49
tatctgggga gtaaaattcc gtacgcgacc ctgaag                36

<210> SEQ ID NO 50
<211> LENGTH: 36
<212> TYPE: DNA
<213> ORGANISM: Artificial Sequence
<220> FEATURE:
<223> OTHER INFORMATION: primer

<400> SEQUENCE: 50
cttcagggtc gcgtacggaa ttttactccc cagata                36

<210> SEQ ID NO 51
<211> LENGTH: 36
<212> TYPE: DNA
<213> ORGANISM: Artificial Sequence
<220> FEATURE:
<223> OTHER INFORMATION: primer

<400> SEQUENCE: 51
tatctgggga gtaaaattta ttacgcgacc ctgaag    36

<210> SEQ ID NO 52
<211> LENGTH: 36
<212> TYPE: DNA
<213> ORGANISM: Artificial Sequence
<220> FEATURE:
<223> OTHER INFORMATION: primer

<400> SEQUENCE: 52
cttcagggtc gcgtaataaa ttttactccc cagata    36

<210> SEQ ID NO 53
<211> LENGTH: 36
<212> TYPE: DNA
<213> ORGANISM: Artificial Sequence
<220> FEATURE:
<223> OTHER INFORMATION: primer

<400> SEQUENCE: 53
tatctgggga gtaaaattca gtacgcgacc ctgaag    36

<210> SEQ ID NO 54
<211> LENGTH: 36
<212> TYPE: DNA
<213> ORGANISM: Artificial Sequence
<220> FEATURE:
<223> OTHER INFORMATION: primer

<400> SEQUENCE: 54
cttcagggtc gcgtactgaa ttttactccc cagata    36

<210> SEQ ID NO 55
<211> LENGTH: 36
<212> TYPE: DNA
<213> ORGANISM: Artificial Sequence
<220> FEATURE:
<223> OTHER INFORMATION: primer

<400> SEQUENCE: 55
tatctgggga gtaaaattaa atacgcgacc ctgaag    36

<210> SEQ ID NO 56
<211> LENGTH: 36
<212> TYPE: DNA
<213> ORGANISM: Artificial Sequence
<220> FEATURE:
<223> OTHER INFORMATION: primer

<400> SEQUENCE: 56
cttcagggtc gcgtatttaa ttttactccc cagata    36

<210> SEQ ID NO 57
<211> LENGTH: 36
<212> TYPE: DNA
<213> ORGANISM: Artificial Sequence
<220> FEATURE:
<223> OTHER INFORMATION: primer

<400> SEQUENCE: 57
tatctgggga gtaaaattga atacgcgacc ctgaag    36

<210> SEQ ID NO 58
<211> LENGTH: 36

<212> TYPE: DNA
<213> ORGANISM: Artificial Sequence
<220> FEATURE:
<223> OTHER INFORMATION: primer

<400> SEQUENCE: 58
cttcagggtc gcgtattcaa ttttactccc cagata        36

<210> SEQ ID NO 59
<211> LENGTH: 36
<212> TYPE: DNA
<213> ORGANISM: Artificial Sequence
<220> FEATURE:
<223> OTHER INFORMATION: primer

<400> SEQUENCE: 59
tatctgggga gtaaaatttg ctacgcgacc ctgaag        36

<210> SEQ ID NO 60
<211> LENGTH: 36
<212> TYPE: DNA
<213> ORGANISM: Artificial Sequence
<220> FEATURE:
<223> OTHER INFORMATION: primer

<400> SEQUENCE: 60
cttcagggtc gcgtagcaaa ttttactccc cagata        36

<210> SEQ ID NO 61
<211> LENGTH: 36
<212> TYPE: DNA
<213> ORGANISM: Artificial Sequence
<220> FEATURE:
<223> OTHER INFORMATION: primer

<400> SEQUENCE: 61
tatctgggga gtaaaatttg gtacgcgacc ctgaag        36

<210> SEQ ID NO 62
<211> LENGTH: 36
<212> TYPE: DNA
<213> ORGANISM: Artificial Sequence
<220> FEATURE:
<223> OTHER INFORMATION: primer

<400> SEQUENCE: 62
cttcagggtc gcgtaccaaa ttttactccc cagata        36

<210> SEQ ID NO 63
<211> LENGTH: 36
<212> TYPE: DNA
<213> ORGANISM: Artificial Sequence
<220> FEATURE:
<223> OTHER INFORMATION: primer

<400> SEQUENCE: 63
tatctgggga gtaaaattcg ttacgcgacc ctgaag        36

<210> SEQ ID NO 64
<211> LENGTH: 36
<212> TYPE: DNA
<213> ORGANISM: Artificial Sequence
<220> FEATURE:
<223> OTHER INFORMATION: primer

<400> SEQUENCE: 64
cttcagggtc gcgtaacgaa ttttactccc cagata       36

<210> SEQ ID NO 65
<211> LENGTH: 36
<212> TYPE: DNA
<213> ORGANISM: Artificial Sequence
<220> FEATURE:
<223> OTHER INFORMATION: primer

<400> SEQUENCE: 65
gggccaaata ccctgtgggt actcaaaaat agcgtc       36

<210> SEQ ID NO 66
<211> LENGTH: 36
<212> TYPE: DNA
<213> ORGANISM: Artificial Sequence
<220> FEATURE:
<223> OTHER INFORMATION: primer

<400> SEQUENCE: 66
gacgctattt ttgagtaccc acagggtatt tggccc       36

<210> SEQ ID NO 67
<211> LENGTH: 36
<212> TYPE: DNA
<213> ORGANISM: Artificial Sequence
<220> FEATURE:
<223> OTHER INFORMATION: primer

<400> SEQUENCE: 67
gggccaaata ccctgctggt actcaaaaat agcgtc       36

<210> SEQ ID NO 68
<211> LENGTH: 36
<212> TYPE: DNA
<213> ORGANISM: Artificial Sequence
<220> FEATURE:
<223> OTHER INFORMATION: primer

<400> SEQUENCE: 68
gacgctattt ttgagtacca gcagggtatt tggccc       36

<210> SEQ ID NO 69
<211> LENGTH: 36
<212> TYPE: DNA
<213> ORGANISM: Artificial Sequence
<220> FEATURE:
<223> OTHER INFORMATION: primer

<400> SEQUENCE: 69
gggccaaata ccctggtggt actcaaaaat agcgtc       36

<210> SEQ ID NO 70
<211> LENGTH: 36
<212> TYPE: DNA
<213> ORGANISM: Artificial Sequence
<220> FEATURE:
<223> OTHER INFORMATION: primer

<400> SEQUENCE: 70
gacgctattt ttgagtacca ccagggtatt tggccc       36

<210> SEQ ID NO 71
<211> LENGTH: 36
<212> TYPE: DNA
<213> ORGANISM: Artificial Sequence
<220> FEATURE:
<223> OTHER INFORMATION: primer

<400> SEQUENCE: 71
gggccaaata ccctgggcgt actcaaaaat agcgtc        36

<210> SEQ ID NO 72
<211> LENGTH: 36
<212> TYPE: DNA
<213> ORGANISM: Artificial Sequence
<220> FEATURE:
<223> OTHER INFORMATION: primer

<400> SEQUENCE: 72
gacgctattt ttgagtacgc ccagggtatt tggccc        36

<210> SEQ ID NO 73
<211> LENGTH: 36
<212> TYPE: DNA
<213> ORGANISM: Artificial Sequence
<220> FEATURE:
<223> OTHER INFORMATION: primer

<400> SEQUENCE: 73
gggccaaata ccctgtctgt actcaaaaat agcgtc        36

<210> SEQ ID NO 74
<211> LENGTH: 36
<212> TYPE: DNA
<213> ORGANISM: Artificial Sequence
<220> FEATURE:
<223> OTHER INFORMATION: primer

<400> SEQUENCE: 74
gacgctattt ttgagtacag acagggtatt tggccc        36

<210> SEQ ID NO 75
<211> LENGTH: 36
<212> TYPE: DNA
<213> ORGANISM: Artificial Sequence
<220> FEATURE:
<223> OTHER INFORMATION: primer

<400> SEQUENCE: 75
gggccaaata ccctgaacgt actcaaaaat agcgtc        36

<210> SEQ ID NO 76
<211> LENGTH: 36
<212> TYPE: DNA
<213> ORGANISM: Artificial Sequence
<220> FEATURE:
<223> OTHER INFORMATION: primer

<400> SEQUENCE: 76
gacgctattt ttgagtacgt tcagggtatt tggccc        36

<210> SEQ ID NO 77
<211> LENGTH: 36
<212> TYPE: DNA
<213> ORGANISM: Artificial Sequence
<220> FEATURE:
<223> OTHER INFORMATION: primer

<400> SEQUENCE: 77
gggccaaata ccctggatgt actcaaaaat agcgtc        36

<210> SEQ ID NO 78
<211> LENGTH: 36
<212> TYPE: DNA
<213> ORGANISM: Artificial Sequence
<220> FEATURE:
<223> OTHER INFORMATION: primer

<400> SEQUENCE: 78
gacgctattt ttgagtacat ccagggtatt tggccc                          36

<210> SEQ ID NO 79
<211> LENGTH: 36
<212> TYPE: DNA
<213> ORGANISM: Artificial Sequence
<220> FEATURE:
<223> OTHER INFORMATION: primer

<400> SEQUENCE: 79
gggccaaata ccctgcatgt actcaaaaat agcgtc                          36

<210> SEQ ID NO 80
<211> LENGTH: 36
<212> TYPE: DNA
<213> ORGANISM: Artificial Sequence
<220> FEATURE:
<223> OTHER INFORMATION: primer

<400> SEQUENCE: 80
gacgctattt ttgagtacat gcagggtatt tggccc                          36

<210> SEQ ID NO 81
<211> LENGTH: 36
<212> TYPE: DNA
<213> ORGANISM: Artificial Sequence
<220> FEATURE:
<223> OTHER INFORMATION: primer

<400> SEQUENCE: 81
gggccaaata ccctgattgt actcaaaaat agcgtc                          36

<210> SEQ ID NO 82
<211> LENGTH: 36
<212> TYPE: DNA
<213> ORGANISM: Artificial Sequence
<220> FEATURE:
<223> OTHER INFORMATION: primer

<400> SEQUENCE: 82
gacgctattt ttgagtacaa tcagggtatt tggccc                          36

<210> SEQ ID NO 83
<211> LENGTH: 36
<212> TYPE: DNA
<213> ORGANISM: Artificial Sequence
<220> FEATURE:
<223> OTHER INFORMATION: primer

<400> SEQUENCE: 83
gggccaaata ccctgccggt actcaaaaat agcgtc                          36

<210> SEQ ID NO 84
<211> LENGTH: 36
<212> TYPE: DNA
<213> ORGANISM: Artificial Sequence
<220> FEATURE:
<223> OTHER INFORMATION: primer -continued

```
<400> SEQUENCE: 84
gacgctattt tgagtaccg gcagggtatt tggccc                                      36

<210> SEQ ID NO 85
<211> LENGTH: 36
<212> TYPE: DNA
<213> ORGANISM: Artificial Sequence
<220> FEATURE:
<223> OTHER INFORMATION: primer

<400> SEQUENCE: 85
gggccaaata ccctgtatgt actcaaaaat agcgtc                                     36

<210> SEQ ID NO 86
<211> LENGTH: 36
<212> TYPE: DNA
<213> ORGANISM: Artificial Sequence
<220> FEATURE:
<223> OTHER INFORMATION: primer

<400> SEQUENCE: 86
gacgctattt tgagtacat acagggtatt tggccc                                      36

<210> SEQ ID NO 87
<211> LENGTH: 36
<212> TYPE: DNA
<213> ORGANISM: Artificial Sequence
<220> FEATURE:
<223> OTHER INFORMATION: primer

<400> SEQUENCE: 87
gggccaaata ccctgcaggt actcaaaaat agcgtc                                     36

<210> SEQ ID NO 88
<211> LENGTH: 36
<212> TYPE: DNA
<213> ORGANISM: Artificial Sequence
<220> FEATURE:
<223> OTHER INFORMATION: primer

<400> SEQUENCE: 88
gacgctattt tgagtacct gcagggtatt tggccc                                      36

<210> SEQ ID NO 89
<211> LENGTH: 36
<212> TYPE: DNA
<213> ORGANISM: Artificial Sequence
<220> FEATURE:
<223> OTHER INFORMATION: primer

<400> SEQUENCE: 89
gggccaaata ccctgaaagt actcaaaaat agcgtc                                     36

<210> SEQ ID NO 90
<211> LENGTH: 36
<212> TYPE: DNA
<213> ORGANISM: Artificial Sequence
<220> FEATURE:
<223> OTHER INFORMATION: primer

<400> SEQUENCE: 90
gacgctattt tgagtactt tcagggtatt tggccc                                      36

<210> SEQ ID NO 91
```

```
<211> LENGTH: 36
<212> TYPE: DNA
<213> ORGANISM: Artificial Sequence
<220> FEATURE:
<223> OTHER INFORMATION: primer

<400> SEQUENCE: 91
gggccaaata ccctggaagt actcaaaaat agcgtc                          36

<210> SEQ ID NO 92
<211> LENGTH: 36
<212> TYPE: DNA
<213> ORGANISM: Artificial Sequence
<220> FEATURE:
<223> OTHER INFORMATION: primer

<400> SEQUENCE: 92
gacgctattt ttgagtactt ccagggtatt tggccc                          36

<210> SEQ ID NO 93
<211> LENGTH: 36
<212> TYPE: DNA
<213> ORGANISM: Artificial Sequence
<220> FEATURE:
<223> OTHER INFORMATION: primer

<400> SEQUENCE: 93
gggccaaata ccctgtgcgt actcaaaaat agcgtc                          36

<210> SEQ ID NO 94
<211> LENGTH: 36
<212> TYPE: DNA
<213> ORGANISM: Artificial Sequence
<220> FEATURE:
<223> OTHER INFORMATION: primer

<400> SEQUENCE: 94
gacgctattt ttgagtacgc acagggtatt tggccc                          36

<210> SEQ ID NO 95
<211> LENGTH: 36
<212> TYPE: DNA
<213> ORGANISM: Artificial Sequence
<220> FEATURE:
<223> OTHER INFORMATION: primer

<400> SEQUENCE: 95
gggccaaata ccctgaccgt actcaaaaat agcgtc                          36

<210> SEQ ID NO 96
<211> LENGTH: 36
<212> TYPE: DNA
<213> ORGANISM: Artificial Sequence
<220> FEATURE:
<223> OTHER INFORMATION: primer

<400> SEQUENCE: 96
gacgctattt ttgagtacgg tcagggtatt tggccc                          36

<210> SEQ ID NO 97
<211> LENGTH: 36
<212> TYPE: DNA
<213> ORGANISM: Artificial Sequence
<220> FEATURE:
<223> OTHER INFORMATION: primer

<400> SEQUENCE: 97
```
gggccaaata ccctgcgtgt actcaaaaat agcgtc                                    36

<210> SEQ ID NO 98
<211> LENGTH: 36
<212> TYPE: DNA
<213> ORGANISM: Artificial Sequence
<220> FEATURE:
<223> OTHER INFORMATION: primer

<400> SEQUENCE: 98
gacgctattt ttgagtacac gcagggtatt tggccc                                    36

<210> SEQ ID NO 99
<211> LENGTH: 36
<212> TYPE: DNA
<213> ORGANISM: Artificial Sequence
<220> FEATURE:
<223> OTHER INFORMATION: primer

<400> SEQUENCE: 99
acgctggaac tggtgagttg gtgctatttg agcttc                                    36

<210> SEQ ID NO 100
<211> LENGTH: 36
<212> TYPE: DNA
<213> ORGANISM: Artificial Sequence
<220> FEATURE:
<223> OTHER INFORMATION: primer

<400> SEQUENCE: 100
gaagctcaaa tagcaccaac tcaccagttc cagcgt                                    36

<210> SEQ ID NO 101
<211> LENGTH: 36
<212> TYPE: DNA
<213> ORGANISM: Artificial Sequence
<220> FEATURE:
<223> OTHER INFORMATION: primer

<400> SEQUENCE: 101
acgctggaac tggtgagtct gtgctatttg agcttc                                    36

<210> SEQ ID NO 102
<211> LENGTH: 36
<212> TYPE: DNA
<213> ORGANISM: Artificial Sequence
<220> FEATURE:
<223> OTHER INFORMATION: primer

<400> SEQUENCE: 102
gaagctcaaa tagcacagac tcaccagttc cagcgt                                    36

<210> SEQ ID NO 103
<211> LENGTH: 36
<212> TYPE: DNA
<213> ORGANISM: Artificial Sequence
<220> FEATURE:
<223> OTHER INFORMATION: primer

<400> SEQUENCE: 103
acgctggaac tggtgagtgt gtgctatttg agcttc                                    36

<210> SEQ ID NO 104
<211> LENGTH: 36
<212> TYPE: DNA

<213> ORGANISM: Artificial Sequence
<220> FEATURE:
<223> OTHER INFORMATION: primer

<400> SEQUENCE: 104
gaagctcaaa tagcacacac tcaccagttc cagcgt					36

<210> SEQ ID NO 105
<211> LENGTH: 36
<212> TYPE: DNA
<213> ORGANISM: Artificial Sequence
<220> FEATURE:
<223> OTHER INFORMATION: primer

<400> SEQUENCE: 105
acgctggaac tggtgagtgg ctgctatttg agcttc					36

<210> SEQ ID NO 106
<211> LENGTH: 36
<212> TYPE: DNA
<213> ORGANISM: Artificial Sequence
<220> FEATURE:
<223> OTHER INFORMATION: primer

<400> SEQUENCE: 106
gaagctcaaa tagcagccac tcaccagttc cagcgt					36

<210> SEQ ID NO 107
<211> LENGTH: 36
<212> TYPE: DNA
<213> ORGANISM: Artificial Sequence
<220> FEATURE:
<223> OTHER INFORMATION: primer

<400> SEQUENCE: 107
acgctggaac tggtgagttc ttgctatttg agcttc					36

<210> SEQ ID NO 108
<211> LENGTH: 36
<212> TYPE: DNA
<213> ORGANISM: Artificial Sequence
<220> FEATURE:
<223> OTHER INFORMATION: primer

<400> SEQUENCE: 108
gaagctcaaa tagcaagaac tcaccagttc cagcgt					36

<210> SEQ ID NO 109
<211> LENGTH: 36
<212> TYPE: DNA
<213> ORGANISM: Artificial Sequence
<220> FEATURE:
<223> OTHER INFORMATION: primer

<400> SEQUENCE: 109
acgctggaac tggtgagtaa ctgctatttg agcttc					36

<210> SEQ ID NO 110
<211> LENGTH: 36
<212> TYPE: DNA
<213> ORGANISM: Artificial Sequence
<220> FEATURE:
<223> OTHER INFORMATION: primer

<400> SEQUENCE: 110
gaagctcaaa tagcagttac tcaccagttc cagcgt					36

<210> SEQ ID NO 111
<211> LENGTH: 36
<212> TYPE: DNA
<213> ORGANISM: Artificial Sequence
<220> FEATURE:
<223> OTHER INFORMATION: primer

<400> SEQUENCE: 111
acgctggaac tggtgagtga ttgctatttg agcttc                              36

<210> SEQ ID NO 112
<211> LENGTH: 36
<212> TYPE: DNA
<213> ORGANISM: Artificial Sequence
<220> FEATURE:
<223> OTHER INFORMATION: primer

<400> SEQUENCE: 112
gaagctcaaa tagcaatcac tcaccagttc cagcgt                              36

<210> SEQ ID NO 113
<211> LENGTH: 36
<212> TYPE: DNA
<213> ORGANISM: Artificial Sequence
<220> FEATURE:
<223> OTHER INFORMATION: primer

<400> SEQUENCE: 113
acgctggaac tggtgagtca ttgctatttg agcttc                              36

<210> SEQ ID NO 114
<211> LENGTH: 36
<212> TYPE: DNA
<213> ORGANISM: Artificial Sequence
<220> FEATURE:
<223> OTHER INFORMATION: primer

<400> SEQUENCE: 114
gaagctcaaa tagcaatgac tcaccagttc cagcgt                              36

<210> SEQ ID NO 115
<211> LENGTH: 36
<212> TYPE: DNA
<213> ORGANISM: Artificial Sequence
<220> FEATURE:
<223> OTHER INFORMATION: primer

<400> SEQUENCE: 115
acgctggaac tggtgagtat ttgctatttg agcttc                              36

<210> SEQ ID NO 116
<211> LENGTH: 36
<212> TYPE: DNA
<213> ORGANISM: Artificial Sequence
<220> FEATURE:
<223> OTHER INFORMATION: primer

<400> SEQUENCE: 116
gaagctcaaa tagcaaatac tcaccagttc cagcgt                              36

<210> SEQ ID NO 117
<211> LENGTH: 36
<212> TYPE: DNA
<213> ORGANISM: Artificial Sequence
<220> FEATURE:

<223> OTHER INFORMATION: primer

<400> SEQUENCE: 117
acgctggaac tggtgagtcc gtgctatttg agcttc                                    36

<210> SEQ ID NO 118
<211> LENGTH: 36
<212> TYPE: DNA
<213> ORGANISM: Artificial Sequence
<220> FEATURE:
<223> OTHER INFORMATION: primer

<400> SEQUENCE: 118
gaagctcaaa tagcacggac tcaccagttc cagcgt                                    36

<210> SEQ ID NO 119
<211> LENGTH: 36
<212> TYPE: DNA
<213> ORGANISM: Artificial Sequence
<220> FEATURE:
<223> OTHER INFORMATION: primer

<400> SEQUENCE: 119
acgctggaac tggtgagtta ttgctatttg agcttc                                    36

<210> SEQ ID NO 120
<211> LENGTH: 36
<212> TYPE: DNA
<213> ORGANISM: Artificial Sequence
<220> FEATURE:
<223> OTHER INFORMATION: primer

<400> SEQUENCE: 120
gaagctcaaa tagcaataac tcaccagttc cagcgt                                    36

<210> SEQ ID NO 121
<211> LENGTH: 36
<212> TYPE: DNA
<213> ORGANISM: Artificial Sequence
<220> FEATURE:
<223> OTHER INFORMATION: primer

<400> SEQUENCE: 121
acgctggaac tggtgagtca gtgctatttg agcttc                                    36

<210> SEQ ID NO 122
<211> LENGTH: 36
<212> TYPE: DNA
<213> ORGANISM: Artificial Sequence
<220> FEATURE:
<223> OTHER INFORMATION: primer

<400> SEQUENCE: 122
gaagctcaaa tagcactgac tcaccagttc cagcgt                                    36

<210> SEQ ID NO 123
<211> LENGTH: 36
<212> TYPE: DNA
<213> ORGANISM: Artificial Sequence
<220> FEATURE:
<223> OTHER INFORMATION: primer

<400> SEQUENCE: 123
acgctggaac tggtgagtaa atgctatttg agcttc                                    36

<210> SEQ ID NO 124
<211> LENGTH: 36
<212> TYPE: DNA
<213> ORGANISM: Artificial Sequence
<220> FEATURE:
<223> OTHER INFORMATION: primer

<400> SEQUENCE: 124
gaagctcaaa tagcatttac tcaccagttc cagcgt                36

<210> SEQ ID NO 125
<211> LENGTH: 36
<212> TYPE: DNA
<213> ORGANISM: Artificial Sequence
<220> FEATURE:
<223> OTHER INFORMATION: primer

<400> SEQUENCE: 125
acgctggaac tggtgagtga atgctatttg agcttc                36

<210> SEQ ID NO 126
<211> LENGTH: 36
<212> TYPE: DNA
<213> ORGANISM: Artificial Sequence
<220> FEATURE:
<223> OTHER INFORMATION: primer

<400> SEQUENCE: 126
gaagctcaaa tagcattcac tcaccagttc cagcgt                36

<210> SEQ ID NO 127
<211> LENGTH: 36
<212> TYPE: DNA
<213> ORGANISM: Artificial Sequence
<220> FEATURE:
<223> OTHER INFORMATION: primer

<400> SEQUENCE: 127
acgctggaac tggtgagttg ctgctatttg agcttc                36

<210> SEQ ID NO 128
<211> LENGTH: 36
<212> TYPE: DNA
<213> ORGANISM: Artificial Sequence
<220> FEATURE:
<223> OTHER INFORMATION: primer

<400> SEQUENCE: 128
gaagctcaaa tagcagcaac tcaccagttc cagcgt                36

<210> SEQ ID NO 129
<211> LENGTH: 36
<212> TYPE: DNA
<213> ORGANISM: Artificial Sequence
<220> FEATURE:
<223> OTHER INFORMATION: primer

<400> SEQUENCE: 129
acgctggaac tggtgagtac ctgctatttg agcttc                36

<210> SEQ ID NO 130
<211> LENGTH: 36
<212> TYPE: DNA
<213> ORGANISM: Artificial Sequence
<220> FEATURE:
<223> OTHER INFORMATION: primer

<400> SEQUENCE: 130
gaagctcaaa tagcaggtac tcaccagttc cagcgt                     36

<210> SEQ ID NO 131
<211> LENGTH: 36
<212> TYPE: DNA
<213> ORGANISM: Artificial Sequence
<220> FEATURE:
<223> OTHER INFORMATION: primer

<400> SEQUENCE: 131
acgctggaac tggtgagtcg ttgctatttg agcttc                     36

<210> SEQ ID NO 132
<211> LENGTH: 36
<212> TYPE: DNA
<213> ORGANISM: Artificial Sequence
<220> FEATURE:
<223> OTHER INFORMATION: primer

<400> SEQUENCE: 132
gaagctcaaa tagcaacgac tcaccagttc cagcgt                     36

<210> SEQ ID NO 133
<211> LENGTH: 212
<212> TYPE: PRT
<213> ORGANISM: Artificial Sequence
<220> FEATURE:
<223> OTHER INFORMATION: Made in lab - substituted LeuE variant

<400> SEQUENCE: 133

Val Phe Ala Glu Tyr Gly Val Leu Asn Tyr Trp Thr Tyr Leu Val Gly
1               5                   10                  15

Ala Ile Phe Ile Val Leu Val Pro Gly Pro Asn Thr Leu Phe Val Leu
            20                  25                  30

Lys Asn Ser Val Ser Ser Gly Met Lys Gly Gly Tyr Leu Ala Ala Cys
        35                  40                  45

Gly Val Phe Ile Gly Asp Ala Val Leu Met Phe Leu Ala Trp Ala Gly
    50                  55                  60

Val Ala Thr Leu Ile Lys Thr Thr Pro Ile Leu Phe Asn Ile Val Arg
65                  70                  75                  80

Tyr Leu Gly Ala Phe Tyr Leu Leu Tyr Leu Gly Ser Lys Ile Val Tyr
                85                  90                  95

Ala Thr Leu Lys Gly Lys Asn Ser Glu Ala Lys Ser Asp Glu Pro Gln
            100                 105                 110

Tyr Gly Ala Ile Phe Lys Arg Ala Leu Ile Leu Ser Leu Thr Asn Pro
        115                 120                 125

Lys Ala Ile Leu Phe Tyr Val Ser Phe Phe Val Gln Phe Ile Asp Val
    130                 135                 140

Asn Ala Pro His Thr Gly Ile Ser Phe Ile Leu Ala Ala Thr Leu
145                 150                 155                 160

Glu Leu Val Ser Phe Cys Tyr Leu Ser Phe Leu Ile Ile Ser Gly Ala
                165                 170                 175

Phe Val Thr Gln Tyr Ile Arg Thr Lys Lys Lys Leu Ala Lys Val Gly
            180                 185                 190

Asn Ser Leu Ile Gly Leu Met Phe Val Gly Phe Ala Ala Arg Leu Ala
        195                 200                 205

Thr Leu Gln Ser
    210

<210> SEQ ID NO 134
<211> LENGTH: 212
<212> TYPE: PRT
<213> ORGANISM: Artificial Sequence
<220> FEATURE:
<223> OTHER INFORMATION: Made in lab - substituted LeuE variant

<400> SEQUENCE: 134

```
Met Phe Ala Glu Tyr Gly Val Leu Asn Tyr Trp Thr Tyr Leu Val Gly
1               5                   10                  15

Ala Ile Phe Ile Val Leu Val Pro Gly Pro Asn Thr Leu Phe Val Leu
            20                  25                  30

Lys Asn Ser Val Ser Ser Gly Met Lys Gly Gly Tyr Leu Ala Ala Cys
        35                  40                  45

Gly Val Phe Ile Gly Asp Ala Val Leu Met Phe Leu Ala Trp Ala Gly
    50                  55                  60

Val Ala Thr Leu Ile Lys Thr Thr Pro Ile Leu Phe Asn Ile Val Arg
65                  70                  75                  80

Tyr Leu Gly Ala Phe Tyr Leu Leu Tyr Leu Gly Ser Lys Ile Val Tyr
                85                  90                  95

Ala Thr Leu Lys Gly Lys Asn Ser Glu Ala Lys Ser Asp Glu Pro Gln
            100                 105                 110

Tyr Gly Ala Ile Phe Lys Arg Ala Leu Ile Leu Ser Leu Thr Asn Pro
        115                 120                 125

Lys Ala Ile Leu Phe Tyr Val Ser Phe Phe Val Gln Phe Ile Asp Val
    130                 135                 140

Asn Ala Pro His Thr Gly Ile Ser Phe Phe Ile Leu Ala Ala Thr Leu
145                 150                 155                 160

Glu Leu Val Ser Phe Cys Tyr Leu Ser Phe Leu Ile Ile Ser Gly Ala
                165                 170                 175

Phe Val Thr Gln Tyr Ile Arg Thr Lys Lys Lys Leu Ala Lys Val Gly
            180                 185                 190

Asn Ser Leu Ile Gly Leu Met Phe Val Gly Phe Ala Ala Arg Leu Ala
        195                 200                 205

Thr Leu Gln Ser
    210
```

<210> SEQ ID NO 135
<211> LENGTH: 639
<212> TYPE: DNA
<213> ORGANISM: Artificial Sequence
<220> FEATURE:
<223> OTHER INFORMATION: Made in lab - substituted LeuE variant

<400> SEQUENCE: 135

```
gtgttcgctg aatacggggt tctgaattac tggacctatc tggttggggc cattttatt      60 gtgttggtgc cagggccaaa taccctgttt gtactcaaaa atagcgtcag tagcggtatg    120
aaaggcggtt atcttgcggc ctgcggtgta tttattggcg atgcggtatt gatgtttctg    180
gcatgggctg gagtggcgac attaattaag accaccccga tattattcaa cattgtacgt    240
tatcttggtg cgttttattt gctctatctg gggagtaaaa ttgtgtacgc gaccctgaag    300
ggtaaaaata gcgaggccaa atccgatgag ccccaatacg gtgctatttt taaacgcgcg    360
ttaattttga gcctgactaa tccgaaagcc attttgttct atgtgtcgtt tttcgtacag    420
tttatcgatg ttaatgcccc acatacggga atttcattct ttattctggc ggcgacgctg    480
```

```
gaactggtga gtttctgcta tttgagcttc ctgattatat ctggtgcttt tgtcacgcag    540
tacatacgta ccaaaaagaa actggctaaa gttggcaact cactgattgg tttgatgttc    600
gtgggtttcg ctgcccgact ggcgacgctg caatcctga                           639
```

<210> SEQ ID NO 136
<211> LENGTH: 639
<212> TYPE: DNA
<213> ORGANISM: Artificial Sequence
<220> FEATURE:
<223> OTHER INFORMATION: Made in lab - substituted LeuE variant

<400> SEQUENCE: 136

```
atgttcgctg aatacggggt tctgaattac tggacctatc tggttggggc cattttta tt    60 gtgttggtgc cagggccaaa taccctgttt gtactcaaaa atagcgtcag tagcggtatg    120
aaaggcggtt atcttgcggc ctgcggtgta tttattggcg atgcggtatt gatgtttctg    180
gcatgggctg gagtggcgac attaattaag accaccccga tattattcaa cattgtacgt    240
tatcttggtg cgttttattt gctctatctg gggagtaaaa ttgtgtacgc gacccctgaag   300 ggtaaaaata gcgaggccaa atccgatgag ccccaatacg gtgctatttt taaacgcgcg    360 ttaatttga gcctgactaa tccgaaagcc atttttgttct atgtgtcgtt tttcgtacag    420
tttatcgatg ttaatgcccc acatacggga atttcattct ttattctggc ggcgacgctg    480
gaactggtga gtttctgcta tttgagcttc ctgattatat ctggtgcttt tgtcacgcag    540
tacatacgta ccaaaaagaa actggctaaa gttggcaact cactgattgg tttgatgttc    600
gtgggtttcg ctgcccgact ggcgacgctg caatcctga                           639
```

<210> SEQ ID NO 137
<211> LENGTH: 212
<212> TYPE: PRT
<213> ORGANISM: Artificial Sequence
<220> FEATURE:
<223> OTHER INFORMATION: Made in lab - substituted LeuE variant

<400> SEQUENCE: 137

```
Val Phe Ala Glu Tyr Gly Val Leu Asn Tyr Trp Thr Tyr Leu Val Gly
1               5                   10                  15

Ala Ile Phe Ile Val Leu Val Pro Gly Pro Asn Thr Leu Ala Val Leu
            20                  25                  30

Lys Asn Ser Val Ser Ser Gly Met Lys Gly Gly Tyr Leu Ala Ala Cys
        35                  40                  45

Gly Val Phe Ile Gly Asp Ala Val Leu Met Phe Leu Ala Trp Ala Gly
    50                  55                  60

Val Ala Thr Leu Ile Lys Thr Thr Pro Ile Leu Phe Asn Ile Val Arg
65                  70                  75                  80

Tyr Leu Gly Ala Phe Tyr Leu Leu Tyr Leu Gly Ser Lys Ile Leu Tyr
                85                  90                  95

Ala Thr Leu Lys Gly Lys Asn Ser Glu Ala Lys Ser Asp Glu Pro Gln
            100                 105                 110

Tyr Gly Ala Ile Phe Lys Arg Ala Leu Ile Leu Ser Leu Thr Asn Pro
        115                 120                 125

Lys Ala Ile Leu Phe Tyr Val Ser Phe Phe Val Gln Phe Ile Asp Val
    130                 135                 140

Asn Ala Pro His Thr Gly Ile Ser Phe Ile Leu Ala Ala Thr Leu
145                 150                 155                 160

Glu Leu Val Ser Phe Cys Tyr Leu Ser Phe Leu Ile Ile Ser Gly Ala
```

-continued

```
                165                 170                 175
Phe Val Thr Gln Tyr Ile Arg Thr Lys Lys Lys Leu Ala Lys Val Gly
            180                 185                 190

Asn Ser Leu Ile Gly Leu Met Phe Val Gly Phe Ala Ala Arg Leu Ala
        195                 200                 205

Thr Leu Gln Ser
    210

<210> SEQ ID NO 138
<211> LENGTH: 212
<212> TYPE: PRT
<213> ORGANISM: Artificial Sequence
<220> FEATURE:
<223> OTHER INFORMATION: Made in lab - substituted LeuE variant

<400> SEQUENCE: 138

Met Phe Ala Glu Tyr Gly Val Leu Asn Tyr Trp Thr Tyr Leu Val Gly
1               5                   10                  15

Ala Ile Phe Ile Val Leu Val Pro Gly Pro Asn Thr Leu Ala Val Leu
            20                  25                  30

Lys Asn Ser Val Ser Ser Gly Met Lys Gly Gly Tyr Leu Ala Ala Cys
        35                  40                  45

Gly Val Phe Ile Gly Asp Ala Val Leu Met Phe Leu Ala Trp Ala Gly
    50                  55                  60

Val Ala Thr Leu Ile Lys Thr Thr Pro Ile Leu Phe Asn Ile Val Arg
65                  70                  75                  80

Tyr Leu Gly Ala Phe Tyr Leu Leu Tyr Leu Gly Ser Lys Ile Leu Tyr
                85                  90                  95

Ala Thr Leu Lys Gly Lys Asn Ser Glu Ala Lys Ser Asp Glu Pro Gln
            100                 105                 110

Tyr Gly Ala Ile Phe Lys Arg Ala Leu Ile Leu Ser Leu Thr Asn Pro
        115                 120                 125

Lys Ala Ile Leu Phe Tyr Val Ser Phe Phe Val Gln Phe Ile Asp Val
    130                 135                 140

Asn Ala Pro His Thr Gly Ile Ser Phe Phe Ile Leu Ala Ala Thr Leu
145                 150                 155                 160

Glu Leu Val Ser Phe Cys Tyr Leu Ser Phe Leu Ile Ile Ser Gly Ala
                165                 170                 175

Phe Val Thr Gln Tyr Ile Arg Thr Lys Lys Lys Leu Ala Lys Val Gly
            180                 185                 190

Asn Ser Leu Ile Gly Leu Met Phe Val Gly Phe Ala Ala Arg Leu Ala
        195                 200                 205

Thr Leu Gln Ser
    210

<210> SEQ ID NO 139
<211> LENGTH: 639
<212> TYPE: DNA
<213> ORGANISM: Artificial Sequence
<220> FEATURE:
<223> OTHER INFORMATION: Made in lab - substituted LeuE variant

<400> SEQUENCE: 139
gtgttcgctg aatacggggt tctgaattac tggacctatc tggttggggc cattttattt     60
gtgttggtgc cagggccaaa taccctggcg gtactcaaaa atagcgtcag tagcggtatg    120
aaaggcggtt atcttgcggc ctgcggtgta tttattggcg atgcggtatt gatgtttctg    180
```

```
gcatgggctg gagtggcgac attaattaag accaccccga tattattcaa cattgtacgt    240
tatcttggtg cgttttattt gctctatctg gggagtaaaa ttctttacgc gaccctgaag    300
ggtaaaaata gcgaggccaa atccgatgag ccccaatacg gtgctatttt taaacgcgcg    360
ttaattttga gcctgactaa tccgaaagcc attttgttct atgtgtcgtt tttcgtacag    420
tttatcgatg ttaatgcccc acatacggga atttcattct ttattctggc ggcgacgctg    480
gaactggtga gtttctgcta tttgagcttc ctgattatat ctggtgcttt tgtcacgcag    540
tacatacgta ccaaaaagaa actggctaaa gttggcaact cactgattgg tttgatgttc    600
gtgggtttcg ctgcccgact ggcgacgctg caatcctga                           639
```

<210> SEQ ID NO 140
<211> LENGTH: 639
<212> TYPE: DNA
<213> ORGANISM: Artificial Sequence
<220> FEATURE:
<223> OTHER INFORMATION: Made in lab - substituted LeuE variant

<400> SEQUENCE: 140

```
atgttcgctg aatacggggt tctgaattac tggacctatc tggttggggc cattttttatt    60 gtgttggtgc cagggccaaa taccctggcg gtactcaaaa atagcgtcag tagcggtatg   120
aaaggcggtt atcttgcggc ctgcggtgta tttattggcg atgcggtatt gatgtttctg   180
gcatgggctg gagtggcgac attaattaag accaccccga tattattcaa cattgtacgt   240
tatcttggtg cgttttattt gctctatctg gggagtaaaa ttctttacgc gaccctgaag   300
ggtaaaaata gcgaggccaa atccgatgag ccccaatacg gtgctatttt taaacgcgcg   360
ttaattttga gcctgactaa tccgaaagcc attttgttct atgtgtcgtt tttcgtacag   420
tttatcgatg ttaatgcccc acatacggga atttcattct ttattctggc ggcgacgctg   480
gaactggtga gtttctgcta tttgagcttc ctgattatat ctggtgcttt tgtcacgcag   540
tacatacgta ccaaaaagaa actggctaaa gttggcaact cactgattgg tttgatgttc   600
gtgggtttcg ctgcccgact ggcgacgctg caatcctga                          639
```

<210> SEQ ID NO 141
<211> LENGTH: 212
<212> TYPE: PRT
<213> ORGANISM: Artificial Sequence
<220> FEATURE:
<223> OTHER INFORMATION: Made in lab - substituted LeuE variant

<400> SEQUENCE: 141

```
Val Phe Ala Glu Tyr Gly Val Leu Asn Tyr Trp Thr Tyr Leu Val Gly
 1               5                  10                  15

Ala Ile Phe Ile Val Leu Val Pro Gly Pro Asn Thr Leu Phe Val Leu
            20                  25                  30

Lys Asn Ser Val Ser Ser Gly Met Lys Gly Gly Tyr Leu Ala Ala Cys
        35                  40                  45

Gly Val Phe Ile Gly Asp Ala Val Leu Met Phe Leu Ala Trp Ala Gly
    50                  55                  60

Val Ala Thr Leu Ile Lys Thr Thr Pro Ile Leu Phe Asn Ile Val Arg
65                  70                  75                  80

Tyr Leu Gly Ala Phe Tyr Leu Leu Tyr Leu Gly Ser Lys Ile Leu Tyr
                85                  90                  95

Ala Thr Leu Lys Gly Lys Asn Ser Glu Ala Lys Ser Asp Glu Pro Gln
            100                 105                 110
```

```
Tyr Gly Ala Ile Phe Lys Arg Ala Leu Ile Leu Ser Leu Thr Asn Pro
            115                 120                 125

Lys Ala Ile Leu Phe Tyr Val Ser Phe Phe Val Gln Phe Ile Asp Val
    130                 135                 140

Asn Ala Pro His Thr Gly Ile Ser Phe Ile Leu Ala Ala Thr Leu
145                 150                 155                 160

Glu Leu Val Ser Ala Cys Tyr Leu Ser Phe Leu Ile Ile Ser Gly Ala
                165                 170                 175

Phe Val Thr Gln Tyr Ile Arg Thr Lys Lys Leu Ala Lys Val Gly
            180                 185                 190

Asn Ser Leu Ile Gly Leu Met Phe Val Gly Phe Ala Ala Arg Leu Ala
        195                 200                 205

Thr Leu Gln Ser
    210

<210> SEQ ID NO 142
<211> LENGTH: 212
<212> TYPE: PRT
<213> ORGANISM: Artificial Sequence
<220> FEATURE:
<223> OTHER INFORMATION: Made in lab - substituted LeuE variant

<400> SEQUENCE: 142

Met Phe Ala Glu Tyr Gly Val Leu Asn Tyr Trp Thr Tyr Leu Val Gly
1               5                   10                  15

Ala Ile Phe Ile Val Leu Val Pro Gly Pro Asn Thr Leu Phe Val Leu
            20                  25                  30

Lys Asn Ser Val Ser Ser Gly Met Lys Gly Gly Tyr Leu Ala Ala Cys
        35                  40                  45

Gly Val Phe Ile Gly Asp Ala Val Leu Met Phe Leu Ala Trp Ala Gly
    50                  55                  60

Val Ala Thr Leu Ile Lys Thr Thr Pro Ile Leu Phe Asn Ile Val Arg
65                  70                  75                  80

Tyr Leu Gly Ala Phe Tyr Leu Leu Tyr Leu Gly Ser Lys Ile Leu Tyr
                85                  90                  95

Ala Thr Leu Lys Gly Lys Asn Ser Glu Ala Lys Ser Asp Glu Pro Gln
            100                 105                 110

Tyr Gly Ala Ile Phe Lys Arg Ala Leu Ile Leu Ser Leu Thr Asn Pro
        115                 120                 125

Lys Ala Ile Leu Phe Tyr Val Ser Phe Phe Val Gln Phe Ile Asp Val
    130                 135                 140

Asn Ala Pro His Thr Gly Ile Ser Phe Ile Leu Ala Ala Thr Leu
145                 150                 155                 160

Glu Leu Val Ser Ala Cys Tyr Leu Ser Phe Leu Ile Ile Ser Gly Ala
                165                 170                 175

Phe Val Thr Gln Tyr Ile Arg Thr Lys Lys Leu Ala Lys Val Gly
            180                 185                 190

Asn Ser Leu Ile Gly Leu Met Phe Val Gly Phe Ala Ala Arg Leu Ala
        195                 200                 205

Thr Leu Gln Ser
    210

<210> SEQ ID NO 143
<211> LENGTH: 639
<212> TYPE: DNA
<213> ORGANISM: Artificial Sequence
<220> FEATURE:
```

<223> OTHER INFORMATION: Made in lab - substituted LeuE variant

<400> SEQUENCE: 143

```
gtgttcgctg aatacggggt tctgaattac tggacctatc tggttggggc catttttatt    60
gtgttggtgc cagggccaaa taccctgttt gtactcaaaa atagcgtcag tagcggtatg   120
aaaggcggtt atcttgcggc ctgcggtgta tttattggcg atgcggtatt gatgtttctg   180
gcatgggctg gagtggcgac attaattaag accaccccga tattattcaa cattgtacgt   240
tatcttggtg cgttttattt gctctatctg gggagtaaaa ttctttacgc gaccctgaag   300
ggtaaaaata gcgaggccaa atccgatgag ccccaatacg gtgctatttt taaacgcgcg   360
ttaattttga gcctgactaa tccgaaagcc attttgttct atgtgtcgtt tttcgtacag   420
tttatcgatg ttaatgcccc acatacggga atttcattct ttattctggc ggcgacgctg   480
gaactggtga gtgcgtgcta tttgagcttc ctgattatat ctggtgcttt tgtcacgcag   540
tacatacgta ccaaaaagaa actggctaaa gttggcaact cactgattgg tttgatgttc   600
gtgggtttcg ctgcccgact ggcgacgctg caatcctga                          639
```

<210> SEQ ID NO 144
<211> LENGTH: 639
<212> TYPE: DNA
<213> ORGANISM: Artificial Sequence
<220> FEATURE:
<223> OTHER INFORMATION: Made in lab - substituted LeuE variant

<400> SEQUENCE: 144

```
atgttcgctg aatacggggt tctgaattac tggacctatc tggttggggc catttttatt    60
gtgttggtgc cagggccaaa taccctgttt gtactcaaaa atagcgtcag tagcggtatg   120
aaaggcggtt atcttgcggc ctgcggtgta tttattggcg atgcggtatt gatgtttctg   180
gcatgggctg gagtggcgac attaattaag accaccccga tattattcaa cattgtacgt   240
tatcttggtg cgttttattt gctctatctg gggagtaaaa ttctttacgc gaccctgaag   300
ggtaaaaata gcgaggccaa atccgatgag ccccaatacg gtgctatttt taaacgcgcg   360
ttaattttga gcctgactaa tccgaaagcc attttgttct atgtgtcgtt tttcgtacag   420
tttatcgatg ttaatgcccc acatacggga atttcattct ttattctggc ggcgacgctg   480
gaactggtga gtgcgtgcta tttgagcttc ctgattatat ctggtgcttt tgtcacgcag   540
tacatacgta ccaaaaagaa actggctaaa gttggcaact cactgattgg tttgatgttc   600
gtgggtttcg ctgcccgact ggcgacgctg caatcctga                          639
```

<210> SEQ ID NO 145
<211> LENGTH: 36
<212> TYPE: DNA
<213> ORGANISM: Artificial Sequence
<220> FEATURE:
<223> OTHER INFORMATION: primer

<400> SEQUENCE: 145

```
ataattaaag aggttaatat gttcgctgaa tacggg                              36
```

```
<210> SEQ ID NO 146
<211> LENGTH: 36
<212> TYPE: DNA
<213> ORGANISM: Artificial Sequence
<220> FEATURE:
<223> OTHER INFORMATION: primer

<400> SEQUENCE: 146
cccgtattca gcgaacatat taacctcttt aattat                               36
```

POLYPEPTIDE HAVING THE ACTIVITY OF EXPORTING O-ACETYL-HOMOSERINE

CROSS-REFERENCE TO RELATED APPLICATIONS

This application is a divisional of application Ser. No. 15/579,188, which is the National Stage of International Application No. PCT/KR2016/005951, filed Jun. 3, 2016, which claims priority to Korean Patent Application No. 10-2015-0079358, filed Jun. 4, 2015. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_059_01US_ST25.txt. The text file is 59 KB, was created on Jul. 17, 2019, and is being submitted electronically via EFS-Web.

TECHNICAL FIELD

The present disclosure relates to a protein having the activity of exporting O-acetylhomoserine and a novel modified protein thereof, a microorganism capable of producing O-acetylhomoserine with enhanced expression of the protein, and a method for producing O-acetylhomoserine using the microorganism.

BACKGROUND ART

Methionine, which can be produced by chemical and biological synthesis, is used as a raw material for the synthesis of infusions and medicines as well as for the synthesis of feed and food additives. Recently, a two-step process for producing L-methionine from an L-methionine precursor, produced via fermentation, by an enzyme conversion reaction was disclosed (International Patent Publication No. WO 2008/013432). International Patent Publication No. WO 2008/013432 discloses that O-succinylhomoserine and O-acetylhomoserine can be used as a methionine precursor in the two-step process, and it is very important to produce methionine precursors in high yield for economical large-scale production of methionine.

LeuE is known as a leucine export protein. As one of the proteins belonging to homoserine/homoserine lactone efflux protein (RhtB) family, LeuE is a protein present in the inner membrane and is known to have the role of exporting leucine and its analogues as a putative uncharacterized transport protein.

In the prior art relating to LeuE, it is known that a purine nucleoside or purine nucleotide can be produced by enhancing an amino acid sequence of leuE (yeaS) gene or a modified amino acid sequence thereof, and the amount of amino acid production can be improved. Additionally, a modified leuE having the activity of exporting cysteine is known.

DISCLOSURE

Technical Problem

The inventors of the present disclosure have made many efforts to improve the production of O-acetylhomoserine, and as a result, they have discovered a protein which has the activity of exporting O-acetylhomoserine and a modified protein thereof, thereby completing the present disclosure.

Technical Solution

An object of the present disclosure is to provide a polypeptide having the activity of exporting O-acetylhomoserine.

Another object of the present disclosure is to provide a polynucleotide which encodes the polypeptide.

Still another object of the present disclosure is to provide a microorganism of the genus *Escherichia* producing O-acetylhomoserine, in which a polypeptide having the activity of exporting O-acetylhomoserine is included or overexpressed.

Still another object of the present disclosure is to provide a method for producing O-acetylhomoserine, which includes: culturing a microorganism of the genus *Escherichia* producing O-acetylhomoserine in a medium; and recovering O-acetylhomoserine from the cultured microorganism or the cultured medium.

Still another object of the present disclosure is to provide a method for producing L-methionine, which includes: culturing the microorganism of the genus *Escherichia* producing O-acetylhomoserine in a medium; and converting the O-acetylhomoserine to L-methionine by treating the cultured microorganism or the cultured medium or the O-acetylhomoserine recovered from the cultured microorganism or the cultured medium with methyl mercaptan and a methionine-converting enzyme.

Advantageous Effects of the Invention

The microorganism of the present disclosure including a modified LeuE or LeuE, which are inner membrane proteins, has enhanced activity of exporting O-acetylhomoserine, and thus the production efficiency of O-acetylhomoserine can be enhanced. Accordingly, the microorganism of the present disclosure can be used for efficient production of O-acetylhomoserine. Additionally, O-acetylhomoserine produced with high efficiency may be used for economical large-scale production of L-methionine.

BEST MODE

To achieve the above objects, an aspect of the present disclosure provides a polypeptide having the activity of exporting O-acetylhomoserine, in which at least one amino acid selected from the group consisting of valine at position 1, phenylalanine at position 30, leucine at position 95, and phenylalanine at position 165 in the amino acid sequence of SEQ ID NO: 1 is substituted with another amino acid.

As used herein, the term "O-acetylhomoserine", which is a specific intermediate material in the methionine biosynthesis pathway of microorganisms, refers to an acetyl derivative of L-homoserine. O-acetylhomoserine is known to be produced by reacting homoserine and acetyl-CoA catalyzed by homoserine acetyltransferase, and it has the formula of $C_6H_{11}NO_4$.

As used herein, the term "peptide having the activity of exporting O-acetylhomoserine" refers to a polypeptide having the function of exporting O-acetylhomoserine in a cell of a microorganism to the outside of the cell. Specifically, the peptide may refer to a LeuE protein having the activity of exporting O-acetylhomoserine and a modified protein thereof, but the peptide is not particularly limited thereto as long as it has the activity of exporting O-acetylhomoserine.

As used herein, with regard to amino acid transporters, the term "LeuE", which is a protein belonging to the homoserine/homoserine lactone efflux protein (RhtB) family, refers to a protein present in the inner membrane, but its exact function is not known. In this regard, the inventors of the present disclosure first confirmed that LeuE specifically exports O-acetylhomoserine.

The LeuE may be a protein derived from a microorganism of the genus *Escherichia*, and specifically LeuE derived from *E. coli*, but any LeuE having the activity of exporting O-acetylhomoserine can be included to the scope of the present disclosure without limitation with regard to the origin of the microorganism.

Specifically, the peptide having the activity of exporting O-acetylhomoserine may be a protein having the amino acid sequence of SEQ ID NO: 1. Additionally, the peptide may be a protein which has an amino acid sequence having the activity of exporting O-acetylhomoserine substantially the same as or equivalent to that of the amino acid sequence of SEQ ID NO: 1, while having a homology of at least 70%, specifically at least 80%, and more specifically at least 90% to the amino acid sequence of SEQ ID NO: 1. Alternatively, the peptide may be an amino acid sequence having such homology where there is deletion, modification, substitution, or addition in part of the amino acid sequence having the activity of exporting O-acetylhomoserine substantially the same as or equivalent to that of the amino acid sequence of SEQ ID NO: 1, and it is obvious that this peptide also belongs to the scope of the present disclosure.

As used herein, the term "modified polypeptide" of the polypeptide having the activity of exporting O-acetylhomoserine refers to a polypeptide that has enhanced activity of exporting O-acetylhomoserine compared to that of native wild-type polypeptide or unmodified polypeptide. Specifically, the modified polypeptide is a peptide which has enhanced activity of exporting O-acetylhomoserine compared to that of the polypeptide which has the amino acid sequence of SEQ ID NO: 1 due to a modification of at least one amino acid in the amino acid sequence of SEQ ID NO: 1.

For example, the modified polypeptide may be a polypeptide in which at least one amino acid selected from the group consisting of valine at position 1, phenylalanine at position 30, leucine at position 95, and phenylalanine at position 165 in the amino acid sequence of SEQ ID NO: 1 is substituted with another amino acid. Specifically, the modified polypeptide may be a polypeptide in which valine at position 1 in the amino acid sequence of SEQ ID NO: 1 is substituted with methionine; phenylalanine at position 30 in the amino acid sequence of SEQ ID NO: 1 is substituted with any one selected from the group consisting of alanine, tryptophan, leucine, valine, glycine, serine, asparagine, aspartic acid, histidine, isoleucine, proline, tyrosine, glutamine, lysine, glutamic acid, cysteine, threonine, and arginine; leucine at position 95 in the amino acid sequence of SEQ ID NO: 1 is substituted with any one selected from the group consisting of valine, phenylalanine, alanine, glycine, threonine, asparagine, aspartic acid, histidine, isoleucine, serine, proline, tyrosine, glutamine, lysine, glutamic acid, cysteine, tryptophan, and arginine; or phenylalanine at position 165 in the amino acid sequence of SEQ ID NO: 1 is substituted with any one selected from the group consisting of alanine, tryptophan, leucine, valine, glycine, serine, asparagine, aspartic acid, histidine, isoleucine, proline, tyrosine, glutamine, lysine, glutamic acid, cysteine, threonine, and arginine. More specifically, the modified polypeptide may be a polypeptide in which valine at position 1 in the amino acid sequence of SEQ ID NO: 1 is substituted with methionine; phenylalanine at position 30 in the amino acid sequence of SEQ ID NO: 1 is substituted with any one selected from the group consisting of alanine, tryptophan, leucine, valine, glycine, serine, asparagine, aspartic acid, and histidine; leucine at position 95 in the amino acid sequence of SEQ ID NO: 1 is substituted with any one selected from the group consisting of valine, phenylalanine, alanine, glycine, threonine, asparagine, aspartic acid, and histidine; or phenylalanine at position 165 in the amino acid sequence of SEQ ID NO: 1 is substituted with any one selected from the group consisting of alanine, tryptophan, leucine, valine, glycine, serine, asparagine, aspartic acid, and histidine. Even more specifically, the modified polypeptide may be a polypeptide in which valine at position 1 in the amino acid sequence of SEQ ID NO: 1 is substituted with methionine; and phenylalanine at position 30, leucine at position 95, and phenylalanine at position 165 in the amino acid sequence of SEQ ID NO: 1 is substituted with another amino acid. Even more specifically, the modified polypeptide may be a polypeptide consisting of an amino acid sequence of SEQ ID NO: 2, 133, 134, 137, 138, 141, or 142. Specifically, the modified polypeptide may be a protein which has an amino acid sequence having enhanced activity of exporting O-acetylhomoserine substantially the same as or equivalent to that of the amino acid sequence of the modified polypeptide, while having a homology of at least 70%, specifically at least 80%, and more specifically at least 90% to the above amino acid sequences. Alternatively, in an amino acid sequence having such homology and having enhanced activity of exporting O-acetylhomoserine substantially the same as or equivalent to that of the amino acid sequence of the modified polypeptide, the amino acid sequence may be one where there is deletion, modification, substitution, or addition in part of the amino acid sequence. The polypeptide is an example of a modified polypeptide of the polypeptide with enhanced activity of exporting O-acetylhomoserine compared to that of the native wild-type polypeptide or unmodified polypeptide, but the polypeptide is not limited thereto. As used herein, the term "natural native state or unmodified state" refers to a state where the introduction of the corresponding polypeptide or the introduction of modification of activity in the present disclosure has not been achieved.

As used herein, the term "homology" refers to the degree of identity between nucleotides or amino acid residues of two amino acid sequences or nucleic acid sequences of a protein-encoding gene determined after aligning them to maximally match with each other for a particular comparison region. When the homology is sufficiently high, the expression products of the corresponding gene may have the same or similar activity. The percentage of the sequence identity can be determined using a known sequence comparison program (e.g., BLAST (NCBI), CLC Main Workbench (CLC bio), MegAlign (DNASTAR Inc), etc.).

An aspect of the present disclosure provides a polynucleotide which encodes the polypeptide having the activity of exporting O-acetylhomoserine. In the present disclosure, the polypeptide having the activity of exporting O-acetylhomoserine is the same as explained above.

For example, the polynucleotide may be one in which the initiation codon is substituted with ATG and may be the nucleotide sequence of SEQ ID NO: 4, 135, 136, 139, 140, 143, or 144 but the nucleotide sequence is not limited thereto. Additionally, with regard to the polynucleotide, the nucleotide sequence and modified nucleotide sequences thereof encoding the same amino acid sequence are also included in the present disclosure based on codon degeneracy. For example, the nucleotide sequence may be modified to have an optimum codon depending on the microorganism being used.

Specifically, the nucleotide sequence may be one which encodes an amino acid sequence having the activity of exporting O-acetylhomoserine substantially the same as or equivalent to that of the above nucleotide sequences, while having a homology of at least 70%, specifically at least 80%, and more specifically at least 90% to the above amino acid sequences. Alternatively, the nucleotide sequence may be a sequence capable of hybridizing with a probe, which can be prepared from a known gene sequence (e.g., a sequence complementary to all or part of the above nucleotide sequences), under stringent conditions to encode a protein having the activity of exporting O-acetylhomoserine. As used herein, the term "stringent condition" refers to a condition in which so-called a specific hybrid is formed while a non-specific hybrid is not formed. For example, the stringent condition may include a condition in which genes having a high homology (e.g., 80% or more, specifically 90% or more, more specifically 95% or more, even more specifically 97% or more, and even more specifically 99% or more) can hybridize between them, whereas genes having a lower homology thereof cannot hybridize with each other; or conditions for conventional southern hybridization (i.e., conditions for washing once, and specifically two or three times under a salt concentration and temperature corresponding to 60° C., 1×SSC, and 0.1% SDS; specifically under 60° C., 0.1×SSC, and 0.1% SDS, and more specifically under 68° C., 0.1×SSC, and 0.1% SDS) (Sambrook et al., *Molecular Cloning: A Laboratory Manual*, 3rd Ed., Cold Spring Harbor Laboratory Press, Cold Spring Harbor, N.Y. (2001)). The probe used for the hybridization may optionally be a part of the nucleotide sequence complementary to the above nucleotide sequences. Such a probe can be prepared by PCR using an oligonucleotide prepared based on a known sequence as a primer and a gene fragment containing such a nucleotide sequence as a template. For example, as the probe, a gene fragment of about 300 bp may be used. More specifically, when a gene fragment of about 300 bp is used as a probe, the conditions of 50° C., 2×SSC, and 0.1% SDS are listed as washing conditions for the hybridization.

The genes used in the present disclosure, the protein sequences and the promoter sequences they encode can be obtained from a known database (e.g., GenBank of NCBI), but are not limited thereto.

An aspect of the present disclosure relates to a microorganism in which the polypeptide having the activity of exporting O-acetylhomoserine or a modified polypeptide thereof is included or overexpressed. Specifically, the microorganism may be a microorganism producing O-acetylhomoserine or a modified polypeptide thereof, in which a polypeptide consisting of the amino acid sequence of SEQ ID NO: 1 is included or overexpressed.

The polypeptide having the activity of exporting O-acetylhomoserine and the modified polypeptide thereof are the same as explained above.

As used herein, the term "microorganism producing O-acetylhomoserine" refers to a microorganism capable of producing O-acetylhomoserine in the microorganism and exporting it to a medium. The activity of producing O-acetylhomoserine can be provided or enhanced by natural or artificial mutations or species improvement. Specifically, those microorganisms which produce O-acetylhomoserine can be included regardless of their microbial origin, as long as they can produce O-acetylhomoserine. In an embodiment, the microorganism may be one belonging to the genus *Escherichia*, and more specifically, *Escherichia coli*.

Meanwhile, in the present disclosure, the microorganisms producing O-acetylhomoserine may be a modified microorganism in which a known modification is additionally introduced with regard to related mechanisms such as homoserine biosynthesis-related pathways and mechanisms related to exporting O-acetylhomoserine, etc. so as to enhance the productivity of O-acetylhomoserine apart from the LeuE.

Another specific embodiment of the present disclosure may relate to the microorganism producing O-acetylhomoserine in which, additionally, the activity of cystathionine synthase is inactivated. Specifically, the microorganism may be one in which the gene encoding cystathionine synthase (metB) is deletion or its expression is weakened compared to that of an unmodified microorganism, but is not limited thereto. The amino acid sequence of the metB gene can be obtained from a known database and any amino acid sequence having the activity of cystathionine synthase can be included without limitation (e.g., a protein having the amino acid sequence of SEQ ID NO: 5). The protein having the amino acid sequence of SEQ ID NO: 5 may be a protein encoded by the nucleotide sequence of SEQ ID NO: 6, but is not limited thereto.

Additionally, still another specific embodiment of the present disclosure may relate to the microorganism producing O-acetylhomoserine in which, additionally, the activity of homoserine kinase is inactivated. Specifically, the microorganism may be one in which the activity of homoserine kinase is reduced compared to its endogenous activity of an unmodified microorganism or is removed. For example, the microorganism may be one in which the gene (thrB) encoding homoserine kinase is linked to a weaker promoter compared to a native promoter, or is modified or deletion to have weak activity, but the promoter is not limited thereto. The amino acid sequence of the thrB gene can be obtained from a known database and any amino acid sequence having the activity of homoserine kinase can be included without limitation (e.g., a protein having the amino acid sequence of SEQ ID NO: 7). The protein having the amino acid sequence of SEQ ID NO: 7 may be a protein encoded by the nucleotide sequence of SEQ ID NO: 8, but is not limited thereto.

As used herein, the term "inactivation" of the protein refers to a case where the activity of the protein of a microorganism is reduced compared to the enzyme activity possessed by the microorganism in a native wild-type protein or unmodified protein; a case where the protein is not expressed at all; or a case where the protein is expressed but exhibits no activity. The inactivation is a concept including a case where the activity of the enzyme itself is reduced or removed compared to the activity of the enzyme originally possessed by the microorganism due to the modification, etc. of the gene encoding the enzyme; a case where the entire activity level of the enzyme in a cell is reduced or removed compared to the activity of the enzyme originally possessed by the wild-type strain of the microorganism due to the inhibition of the expression or translation of the gene encoding the enzyme; a case where part or the entirety of the gene is deleted; and a combination thereof; but the inactivation is not limited thereto.

The inactivation of an enzyme may be achieved by applying various methods well known in the art. Examples of the methods may include a method of substituting the gene encoding the enzyme on the chromosome with a gene modified to reduce the activity of the enzyme, including the case when the enzyme activity is removed; a method of introducing a modification in the expression control sequence of the gene encoding the enzyme on the chromosome; a method of substituting the expression control sequence of the gene encoding the enzyme with a sequence having weak or no activity; a method of deleting part or the entirety of the gene encoding the enzyme on the chromosome; a method of introducing an antisense oligonucleotide (e.g., antisense RNA) which binds complementary to a transcript of the gene on the chromosome, thereby inhibiting the translation from the mRNA into the enzyme; a method of artificially incorporating a sequence complementary to the SD sequence into the upstream of the SD sequence of the gene encoding the enzyme, forming a secondary structure, thereby making the attachment of ribosome thereto impossible; a method of incorporating a promoter to the 3' terminus of the open reading frame (ORF) to induce a reverse transcription (reverse transcription engineering (RTE)), etc., and also a combination thereof, but the methods are not particularly limited thereto.

The method of modifying the expression control sequence may be performed by inducing a modification of the expression control sequence by deletion, insertion, non-conservative or conservative substitution, or a combination thereof in the nucleic acid sequence of the expression control sequence so as to further weaken the activity of the expression control sequence; or by substituting with a nucleic acid having weaker activity. The expression control sequence may include a promoter, an operator sequence, a sequence encoding a ribosome-binding region, and sequences controlling the termination of transcription and translation, but is not limited thereto.

Furthermore, the gene sequence on the chromosome may be modified by inducing a modification in the sequence by deletion, insertion, non-conservative or conservative substitution, or a combination thereof in the gene sequence for further weakening the enzyme activity; or by substituting with a gene sequence which was improved to have weaker activity or a gene sequence which was improved to have no activity, but the method is not limited thereto.

Additionally, the method of deleting part or the entirety of a gene encoding an enzyme may be performed by substituting the polynucleotide encoding the endogenous target protein within the chromosome with a polynucleotide or marker gene having a partial deletion in the nucleic acid sequence using a vector for chromosomal insertion within a bacterial strain. In an exemplary embodiment of the method of deleting part or the entirety of a gene, a method for deleting a gene by homologous recombination may be used, but the method is not limited thereto.

As used herein, the term "part" may vary depending on the kinds of polynucleotides, and it may specifically refer to 1 to 300, more specifically 1 to 100, and even more specifically 1 to 50, but is not particularly limited thereto.

As used herein, the term "homologous recombination" refers to genetic recombination that occurs via crossover at genetic chain loci having a mutual homology.

Furthermore, still another specific embodiment of the present disclosure may relate to the microorganism producing O-acetylhomoserine in which, additionally, the activity of homoserine acetyltransferase is enhanced compared to that of an unmodified microorganism. Specifically, the microorganism may be one in which the activity of homoserine acetyltransferase is enhanced compared to that of an unmodified microorganism, and particularly, may be one in which a modified metA gene encoding homoserine acetyltransferase with enhanced activity is introduced. The modified metA gene may be a gene encoding one in which the 111th amino acid of homoserine acetyltransferase is substituted with glutamic acid and the 112th amino acid of homoserine acetyltransferase is substituted with histidine, but is not limited thereto. The modified metA gene may include without limitation any amino acid sequence having enhanced activity of homoserine acetyltransferase compared to that of its wild-type, and for example, may be a protein having the amino acid sequence of SEQ ID NO: 10. Embodiments of the preparation of the modified metA gene and use thereof, a strain having enhanced activity of homoserine acetyltransferase, etc. are disclosed in Korean Patent No. 10-1335841, and the entire specification of the patent may be incorporated herein as a reference for the present disclosure.

Additionally, still another specific embodiment of the present disclosure may relate to a microorganism producing O-acetylhomoserine belonging to the genus *Escherichia* in which, additionally, the activity of aspartate semialdehyde dehydrogenase, pyridine nucleotide transhydrogenase, or a combination thereof is enhanced compared to that of an unmodified microorganism.

Additionally, still another specific embodiment of the present disclosure may relate to a microorganism producing O-acetylhomoserine in which, additionally, the activity of phosphoenolpyruvate carboxylase, aspartate aminotransferase, or a combination thereof is enhanced compared to that of an unmodified microorganism. As used herein, the term "enhancement" refers to enhancing the activity level of a protein possessed by a microorganism. Enhancement of the activity of a protein is not limited as long as it can enhance the activity of each protein compared to that of the native wild-type protein or unmodified protein, as in the enhancement of the activity of a target protein. The enhancement may be performed by a method selected from the group consisting of i) a method of increasing the copy number of a polynucleotide encoding each protein, ii) a method of introducing a modification in the expression control sequence for increasing the expression of the polynucleotide, iii) a method of modifying the polynucleotide sequence on the chromosome for enhancing the activity of each protein, and iv) a combination thereof. Specifically, the enhancement may be performed by a method selected from the group consisting of a method of inserting a polynucleotide including a nucleotide sequence encoding each protein into the chromosome, a method of introducing the polynucleotide into a microorganism after introducing it into a vector system, a method of introducing a promoter with enhanced activity into an upstream region of the nucleotide sequence encoding each protein or introducing each protein with a modification on its promoter, a method of modifying the nucleotide sequence in the 5'-UTR region, and a method of introducing a modified nucleotide sequence of the nucleotide sequence encoding each protein, but the methods of enhancement are not limited thereto.

Still another aspect of the present disclosure relates to a method for producing O-acetylhomoserine including culturing the microorganism of the genus *Escherichia* producing O-acetylhomoserine in a medium.

Specifically, the above method relates to a method for producing O-acetylhomoserine including culturing the microorganism of the genus *Escherichia* producing O-acetylhomoserine in a medium, and recovering O-acetylhomoserine from the cultured microorganism or the cultured medium.

As used herein, the term "culture" refers to growing a microorganism in an appropriately-adjusted environment. In the present disclosure, the culture process may be performed using an appropriate medium and culture conditions well known in the art. The culture process may be easily adjusted for use by one of ordinary skill in the art according to the strain being selected. The culture may be performed in a batch process, continuous culture, fetch-batch culture, etc. known in the art, but is not particularly limited thereto. The medium and other culture conditions used for culturing the microorganism of the present disclosure may not be particularly limited, but any medium conventionally used for culturing microorganisms of the genus *Escherichia* may be used. Specifically, the microorganism of the present disclosure may be cultured under an aerobic condition in a common medium containing an appropriate carbon, nitrogen, and phosphorus sources, inorganic compounds, amino acids, and/or vitamins, etc., while adjusting temperature, pH, etc.

In the present disclosure, the carbon sources may include carbohydrates such as glucose, fructose, sucrose, maltose, mannitol, sorbitol, etc.; alcohols such as sugar alcohol, glycerol, etc.; organic acids such as pyruvic acid, lactic acid, citric acid, etc.; amino acids such as glutamic acid, methionine, lysine, etc., but the carbon sources are not limited thereto. Additionally, natural organic nutrients such as starch hydrolysate, molasses, blackstrap molasses, rice bran, cassava, sugar cane bagasse, corn steep liquor, etc. may be used. Specifically, carbohydrates such as glucose and sterilized pretreated molasses (i.e., molasses converted to reducing sugar) may be used, and additionally, various other carbon sources in an appropriate amount may be used without limitation. These carbon sources may be used alone or in a combination of at least two kinds.

Examples of the nitrogen sources may include inorganic nitrogen sources (e.g., ammonia, ammonium sulfate, ammonium chloride, ammonium acetate, ammonium phosphate, ammonium carbonate, ammonium nitrate, etc.); amino acids (glutamic acid, methionine, glutamine, etc.); and organic nitrogen sources (e.g., peptone, N-Z amine, meat extract, yeast extract, malt extract, corn steep liquor, casein hydrolysate, fish or decomposition product thereof, defatted soybean cake or decomposition product thereof, etc.). These nitrogen sources may be used alone or in a combination of at least two kinds, but are not limited thereto.

Examples of the phosphorus sources may include monopotassium phosphate, dipotassium phosphate, and sodium-containing salts corresponding thereto. Examples of inorganic compounds to be used may include sodium chloride, calcium chloride, iron chloride, magnesium sulfate, iron sulfate, manganese sulfate, calcium carbonate, etc. Additionally, amino acids, vitamins, and/or appropriate precursors may be included, but are not limited thereto. These media or precursors may be added in a batch culture process or continuous culture process to a culture, but are not limited thereto.

During the culture period in the present disclosure, the pH of a culture may be adjusted by adding a compound such as ammonium hydroxide, potassium hydroxide, ammonia, phosphoric acid, sulfuric acid, etc. to the culture in an appropriate manner. Additionally, during the culture period, an antifoaming agent, such as fatty acid polyglycol ester, may be added to prevent foam generation. Additionally, for maintaining the aerobic state of the culture, oxygen or an oxygen-containing gas may be injected into the culture, while for maintaining the anaerobic and microaerobic states of the culture, nitrogen, hydrogen, or carbon dioxide gas may be injected without the injection of air.

The culture temperature may normally be from 27° C. to 37° C., and specifically from 30° C. to 35° C., but the culture temperature is not limited thereto. Additionally, the culture may be continued until the production of desired material(s) can be obtained, and specifically for 10 hours to 100 hours, but is not limited thereto.

The recovery of O-acetylhomoserine may be performed using the method of culturing a microorganism of the present disclosure. For example, the target O-acetylhomoserine can be recovered from a culture using an appropriate method known in the art (e.g., a batch-type culture, continuous culture, or fed-batch culture, etc.). For example, methods such as centrifugation, filtration, anion exchange chromatography, crystallization, HPLC, etc. may be used, and additionally, a combined method of appropriate methods known in the art may be used.

The recovery process may include a separation process and/or a purification process.

An aspect of the present disclosure relates to a method for producing L-methionine, which includes culturing the microorganism of the genus *Escherichia* producing O-acetylhomoserine in a medium; and converting the O-acetylhomoserine to L-methionine by treating the cultured microorganism or the cultured medium or the O-acetylhomoserine recovered from the cultured microorganism or the cultured medium with methyl mercaptan and a methionine-converting enzyme.

For example, methionine can be produced from O-acetylhomoserine, which is recovered from a culture of a microorganism of the genus *Escherichia* producing O-acetylhomoserine in a medium, by a two-step process (Korean Patent No. 10-0905381).

The two-step process includes a process of producing L-methionine and an organic acid by an enzyme reaction using an enzyme having the activity of converting O-acetylhomoserine to methionine using O-acetylhomoserine and methyl mercaptan as substrates or a strain containing the enzyme.

The methionine-converting enzyme includes all of the enzymes that convert O-acetylhomoserine to methionine, and particularly O-acetylhomoserine sulfhydrylase, but is not limited thereto.

Specifically, the O-acetylhomoserine sulfhydrylase to be used may be one derived from microbial strains belonging to the genus *Leptospira*, the genus *Chromobacterium*, and the genus *Hyphomonas*, and more specifically, one derived from microbial strains belonging to the genus *Leptospira meyeri*, *Pseudomonas aurogenosa*, *Hyphomonas neptunium*, and *Chromobacterium violaceum*.

The above reaction is shown below:

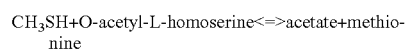

Such additional process of producing methionine is disclosed in Korean Patent No. 10-0905381, and the entire specification of the patent may be included as a reference for the present disclosure.

DETAILED DESCRIPTION OF THE INVENTION

Hereinafter, the present disclosure will be described in detail through exemplary embodiments. However, these exemplary embodiments are provided for the purpose of illustration only and are not intended to limit the scope of the present disclosure.

Reference Example 1: Preparation of Strains Producing O-Acetylhomoserine 1-1. Deletion of metB Gene in Wild-Type E. coli To produce strains producing O-acetylhomoserine, E. coli, which is a representative microorganism among the microorganisms of the genus Escherichia, was used. For this purpose, E. coli K12 W3110 (ATCC 27325), a wild-type E. coli, was obtained from the American Type Culture Collection (ATCC) and used. A strain which has defects in the metB gene (SEQ ID NO: 6) encoding cystathionine gamma synthase and the thrB gene (SEQ ID NO: 8) encoding homoserine kinase in E. coli K12 W3110 strain was prepared. The thus-prepared strain producing O-acetylhomoserine was named W3-BT. An embodiment with regard to the deletion of metB and thrB genes deletion strains is disclosed in Korean Patent No. 10-0905381 or International Patent Publication WO 2008/013432 (see particularly, Examples 1-1 and 1-2 of Korean Patent No. 10-0905381), and the entire specification of the patent may be included herein as a reference for the present disclosure.

1-2. Preparation of Strain Introduced with Modified metA Gene Having Activity of Homoserine Acetyltransferase To enhance the activity of homoserine acetyltransferase in the strain obtained in Reference Example 1-1, it was attempted to introduce the modified metA gene (SEQ ID NO: 10) encoding homoserine acetyltransferase having enhanced activity into the strain. In an attempt to prepare such a strain, a pCL_Pcj1_metA (EH) plasmid was prepared by the method described in Examples 1 and 3 of Korean Patent No. 10-1335841.

Then, to prepare a replacement cassette as a way to substitute the above-prepared modified metA gene by introducing it into the strain, PCR was performed using the pKD3 vector as a template along with primers of SEQ ID NO: 23 and SEQ ID NO: 24. Specifically, PCR was repeatedly performed for a total of 30 cycles, in which denaturation was performed at 94° C. for 30 seconds, annealing at 55° C. for 30 seconds, and extension at 72° C. for 2 minutes.

For the metA (EH) portion of the replacement cassette, PCR was performed using pCL-Pcj1-metA (EH) as the template along with primers of SEQ ID NO: 19 and SEQ ID NO: 20, whereas, for the metA wild-type portion, primers of SEQ ID NO: 21 and SEQ ID NO: 22 were used, and thereby the respective PCR products were obtained. Based on 3 PCR products, the metA (EH) replacement cassette containing a chloramphenicol marker was prepared using the primers of SEQ ID NO: 19 and SEQ ID NO: 22, and introduced by electroporation into the W3-BT strain, which was transformed with the pKD46 vector, prepared in Reference Example 1-1.

The strains which were confirmed to have been introduced by the above process were again transformed with the pCP 20 vector and cultured in LB medium. The strain in which the chloramphenicol marker was removed and the metA gene was replaced with metA (EH) was named as W3-BTA.

An embodiment with regard to the strain with enhanced activity of homoserine acetyltransferase, etc. is disclosed in Korean Patent No. 10-1335841 or International Patent Publication WO 2012/087039, and the entire specification of the patent may be included herein as a reference for the present disclosure.

1-3. Preparation of Strain Including 2 Copies of ppc, aspC, and Asd Genes

To increase the productivity of O-acetylhomoserine of the W3-BTA strain prepared in Reference Example 1-2, a known strategy of enhancing the biosynthetic pathway was introduced. An attempt was made to prepare strains in which the genes, which are associated with phosphoenolpyruvate carboxylase involved in the biosynthesis of oxaloacetate from phosphoenolpyruvate, aspartate aminotransferase involved in the biosynthesis of aspartate from oxaloacetate, and aspartate-semialdehyde dehydrogenase involved in the biosynthesis of homoserine from β-aspartyl phosphate were amplified to 2 copies, that is, ppc, aspC, and asd genes, were amplified to 2 copies.

For the preparation of the strains, pSG-2ppc, pSG-2aspC, and pSG-2asd plasmids were prepared by the method disclosed in Examples 1-1 to 1-3 of Korean Patent No. 10-1117012, the above plasmids were introduced into the W3-BTA strain, and the strain in which the 3 different genes were sequentially amplified to 2 copies was prepared by the method described in Example 1-5 of the Korean patent. The thus-prepared strain was named as W3-BTA2PCD (=WCJM).

An embodiment with regard to the strain with enhanced activity of phosphoenolpyruvate carboxylase, aspartate aminotransferase, and aspartate-semialdehyde dehydrogenase, etc., is disclosed in Korean Patent No. 10-0905381 or International Patent Publication WO 2008/013432, and the entire specification of the patent may be included herein as a reference for the present disclosure.

1-4. Flask Culture Experiment

To test the amount of O-acetylhomoserine production in the strains prepared in Reference Examples 1-2 and 1-3, Erlenmeyer flask culture was performed. W3110, W3-BTA, and WCJM strains were seeded in LB medium and cultured at 33° C. overnight. Single colonies were seeded in 3 mL of LB medium and incubated at 33° C. for 5 hours, diluted 200-fold in a 250 mL Erlenmeyer flask containing 25 mL of medium for producing O-acetylhomoserine, and incubated again at 33° C. at 200 rpm for 30 hours, and the amount of O-acetylhomoserine production was confirmed by HPLC analysis. The composition of the medium used is summarized in Table 1 below.

TABLE 1

Composition of flask medium producing O-acetylhomoserine

| Composition | Concentration (per Liter) |
| --- | --- |
| Glucose | 40 g |
| Ammonium Sulfate | 17 g |
| $KH_2PO_4$ | 1.0 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| $ZnSO_4$ | 5 mg |
| Calcium Carbonate | 30 g |
| Yeast Extract | 2 g |
| Methionine | 0.15 g |
| Threonine | 0.15 g |

The amount of O-acetylhomoserine production was confirmed by HPLC analysis after culturing for 30 hours using the above medium, and the results are summarized in Table 2 below.

TABLE 2

O-Acetylhomoserine production by flask culture

|  | OD (562 nm) | Glucose Consumption (g/L) | O-AH (g/L) |
|---|---|---|---|
| W3110 | 14.2 | 40 | 0 |
| W3-BTA | 8.4 | 36 | 0.9 |
| WCJM | 9.6 | 35 | 1.2 |

As can be seen in Table 2 above, O-acetylhomoserine was not produced at all in the wild-type strain W3110, however, the W3-BTA strain produced O-acetylhomoserine (O-AH) at a concentration of 0.9 g/L in, and the WCJM strain with an enhanced biosynthetic pathway produced O-acetylhomoserine (O-AH) at a concentration of 1.2 g/L.

Example 1: Selection of Membrane Proteins Increasing O-Acetylhomoserine Productivity The inventors of the present disclosure made an attempt to apply LeuE (SEQ ID NO: 1) derived from *Escherichia coli*, which was disclosed as a membrane protein but has not been disclosed with regard to the activity of exporting O-acetylhomoserine and producing O-acetylhomoserine, to O-acetylhomoserine production.

In order to enhance the leuE gene in the strain, the leuE gene was cloned using a SmaI restriction site of the pCL vector.

First, to prepare the leuE gene, PCR was performed for a total of 30 cycles using primers of SEQ ID NOS: 11 and 12, in which denaturation was performed at 94° C. for 30 seconds, annealing at 55° C. for 30 seconds, and extension at 68° C. for 1 minute. The resulting PCR product was electrophoresed on a 1.0% agarose gel and DNA was purified from the 800 bp band. The purified DNA was treated with restriction enzyme SmaI at 37° C. overnight, and after additional purification, leuE gene and the pCL vector were cloned using T4 ligase. After transforming *E. coli* DH5 using the cloned plasmid, the transformed *E. coli* DH5 were selected on LB plate medium containing spectinomycin (50 µg/mL) to obtain the plasmid. The thus-prepared plasmid was introduced into W3-BTA and WCJM strains, which are strains producing O-acetylhomoserine. They were named as W3-BTA/pCL-leuE and WCJM/pCL-leuE, respectively, and flask evaluation on their productivity of O-acetylhomoserine was performed.

Additionally, as the control groups, the empty vector pCL1920 was introduced into W3-BTA and WCJM strains in the same method as described above, and named as W3-BTA/pCL1920 and WCJM pCL1920, respectively, and flask evaluation on their productivity of O-acetylhomoserine was performed.

Specifically, each strain was plated on LB solid medium and cultured overnight in a 33° C. incubator. A single colony of the strain cultured overnight in LB plate medium was seeded in 3 mL of LB medium and incubated at 33° C. for 5 hours, diluted 200-fold in a 250 mL Erlenmeyer flask containing 25 mL of medium for producing O-acetylhomoserine, and incubated again at 33° C. at 200 rpm for 30 hours, and the amount of O-acetylhomoserine production was confirmed by HPLC analysis. The results are summarized in Table 3 below.

TABLE 3

Measurement of O-acetylhomoserine production by flask culture

|  | OD (562 nm) | Glucose Consumption (g/L) | O-AH (g/L) |
|---|---|---|---|
| W3-BTA/pCL1920 | 9.5 | 35 | 0.9 |
| W3-BTA/pCL-leuE | 8.2 | 36 | 1.0 |
| WCJM/pCL1920 | 9.6 | 35 | 1.2 |
| WCJM/pCL-leuE | 8.4 | 36 | 1.5 |

As can be seen in Table 3 above, the WCJM strain introduced with leuE plasmid showed a lower OD compared to that of the control strain introduced with the empty vector, and the WCJM strain also showed higher glucose consumption. However, the WCJM strain produced O-acetylhomoserine at a concentration of 1.5 g/L, and this could not confirm that the increase of O-acetylhomoserine production was due to the introduction of the wild-type leuE. Nevertheless, the results of being capable of controlling OD and increase of glucose consumption rate confirmed the potential exporting activity of the strain. Accordingly, an attempt was made to select modified strains having enhanced activity of exporting O-acetylhomoserine compared to that of the wild-type strain through structural modeling.

Example 2: Preparation of Plasmid with Modification of Start Codon of leuE and Evaluation of O-Acetyl Homoserine Productivity The start codon of wild-type leuE is known to be gtg, which encodes valine, an amino acid. To confirm the enhanced effect of leuE protein by changing the start codon to atg (i.e., a methionine-encoding codon), an experiment to change the start codon based on the plasmid prepared in Example 1 was performed. Specifically, the first amino acid in the amino acid sequence of SEQ ID NO: 1 was substituted with methionine to enhance the activity of exporting O-acetylhomoserine. More specifically, a leuE(ATG) modification was prepared. To prepare the leuE(ATG) modification, primers of SEQ ID NO: 145 and SEQ ID NO: 146 were used, and a modified leuE(ATG) gene was prepared by site-specific mutagenesis (site-directed mutagenesis kit, Stratagene, USA). The existing wild-type plasmid was named as WT, and the initiation codon variant plasmid was named WT_ATG, and the thus-prepared plasmid was introduced to the WCJM strain and the flask evaluation on its productivity of O-acetylhomoserine was performed.

Specifically, each strain was plated on LB solid medium and cultured overnight in a 33° C. incubator. The strain cultured overnight in LB plate medium was seeded in 25 mL titer medium and incubated at 33° C. at 200 rpm for 40 hours. The results are summarized in Table 4 below.

TABLE 4

Measurement of O-acetylhomoserine production by flask culture

|  | OD (562 nm) | Glucose Consumption (g/L) | O-AH (g/L) |
|---|---|---|---|
| WCJM/pCL-leuE WT | 8.4 | 36 | 1.5 |
| WCJM/pCL-leuE WT(ATG) | 7.6 | 39 | 2.6 |

As can be seen in Table 4 above, the strain introduced with the pCL-leuE WT(ATG) plasmid having the start-codon modification showed a lower OD compared to that of the wild-type strain but showed more rapid glucose consumption. The strain introduced with the pCL-leuE WT(ATG) plasmid having the start-codon modification produced O-acetylhomoserine at a concentration of 2.6 g/L, which is an increase of productivity as much as 173% compared to that of the wild-type strain.

Example 3: Preparation of leuE-Modified Plasmid and Evaluation of Productivity of O-Acetylhomoserine 3-1. Preparation of leuE-modified plasmid Experiments to prepare each of the three modified polypeptides which were expected to have a stronger exporting activity compared to that of the wild-type leuE based on the two kinds of plasmids, i.e., plasmid pCL-leuE WT and pCL-leuE WT(ATG) prepared in Examples 1 and 2, were performed. Specifically, the positions of leuE modification were selected via structure modeling to enhance the activity of exporting O-acetylhomoserine, and the amino acids at positions 30, 95, and 165 in the amino acid sequences of SEQ ID NOS: 1 and 2 were substituted with different amino acids, respectively.

More specifically, L95V, F30A, and F165A modifications were prepared. For the preparation of L95V modification, primers of SEQ ID NOS: 13 and 14 were used; for F30A modification, primers of SEQ ID NOS: 25 and 26 were used; and for F165A modification, primers of SEQ ID NOS: 27 and 28 were used. Modified leuE genes were prepared using site-directed mutagenesis kit (Stratagene, USA) along with each of the primer sets described above. Based on the existing wild-type plasmid WT, the modified plasmid L95V was named as WT_M3; the modified plasmid F30A as WT_M4, and the modified plasmid F165A as WT_M6, respectively. Additionally, based on the plasmid with a start codon modification (i.e., WT(ATG)), the modified plasmid L95V was named as WT(ATG) M3, the modified plasmid F30A as WT(ATG) M4, and the modified plasmid F165A as WT(ATG) M6, respectively. The thus-prepared modified plasmids were introduced into the WCJM strain to evaluate the productivity of O-acetylhomoserine in a flask.

Specifically, each strain was plated on LB plate medium and cultured in a 33° C. incubator overnight. The strain cultured overnight in LB solid medium was inoculated into a 25 mL of the titer medium, and then cultured in an incubator at 33° C. incubator at 200 rpm for 40 hours. The results are shown in Table 5 below.

TABLE 5

Measurement of O-acetylhomoserine production by flask culture

|  | OD (562 nm) | Glucose Consumption (g/L) | O-AH (g/L) |
| --- | --- | --- | --- |
| WCJM/pCL1920 | 9.6 | 35 | 1.3 |
| WCJM/pCL-leuE WT | 8.4 | 36 | 1.5 |
| WCJM/pCL-leuE WT_M3 | 8.2 | 38 | 2.3 |
| WCJM/pCL-leuE WT_M4 | 7.9 | 38 | 3.7 |
| WCJM/pCL-leuE WT_M6 | 8.0 | 39 | 4.8 |
| WCJM/pCL-leuE WT(ATG) | 7.6 | 39 | 2.6 |
| WCJM/pCL-leuE WT(ATG)_M3 | 7.5 | 40 | 3.1 |
| WCJM/pCL-leuE WT(ATG)_M4 | 7.3 | 39 | 3.6 |
| WCJM/pCL-leuE WT(ATG)_M6 | 7.5 | 40 | 4.9 |

As can be seen in Table 5 above, all of the 3 strains introduced with the leuE-modified plasmid showed a decrease in OD compared to that of the wild-type, but all of the 3 strains showed more rapid glucose consumption compared to that of the wild-type strain, and in particular, the WT(ATG) M6 strain was shown to produce O-acetylhomoserine at a concentration of 4.9 g/L, thus showing the highest productivity of O-acetylhomoserine. Accordingly, it was confirmed that all of the 3 modified strains of the present disclosure exhibited enhanced productivity of O-acetylhomoserine. Additionally, it was confirmed that when the amount of protein expression was increased by modifying the start codon of leuE, the productivity of O-acetylhomoserine was further enhanced.

3-2. Preparation of Biosynthesis Pathway Genes and Modified Plasmids

To maximize the productivity of O-acetylhomoserine, a plasmid capable of enhancing the biosynthetic pathway to homoserine was prepared. For the cloning of aspartate semialdehyde dehydrogenase, pyridine nucleotide transhydrogenase, and wild-type LeuE and modified LeuE into the pCL vector, asd and pntAB genes were first introduced into the pCL vector.

First, in obtaining the asd and pntAB genes, the PCR was performed for a total of 30 cycles, in which denaturation was performed at 94° C. for 30 seconds, annealing at 55° C. for 30 seconds, and extension at 68° C. for 3 minutes, using primers of SEQ ID NOS: 15 and 16 for asd gene and primers of SEQ ID NOS: 17 and 18 for pntAB gene. The resulting PCR products were electrophoresed on a 1.0% agarose gel and the DNAs respectively obtained from 1.4 kb (asd) and 3 kb (pntAB) sized bands were purified.

The purified two genes were ligated using the sewing PCR (a technique in which the overlapping parts of two genes are ligated first without using any primer and then amplified using the primers at both ends). The conditions for the sewing PCR were performing the PCR described above for 10 cycles and then performing PCR for 20 cycles after adding primers of SEQ ID NOS: 15 and 18. As a result, combined fragments of asd-pntAB genes were prepared, and purified by electrophoresis. The purified fragments and the pCL vector were treated with SmaI at 37° C. overnight, purified further, and the pCL-asd-pntAB plasmid was prepared using T4 ligase.

The leuE gene was cloned into the thus-prepared plasmid. In cloning, specifically, to obtain the leuE gene, PCR was performed for a total of 30 cycles, in which denaturation was performed at 94° C. for 30 seconds, annealing at 55° C. for 30 seconds, and extension at 68° C. for 1 minute, using primers of SEQ ID NOS: 29 and 30.

The resulting PCR product was electrophoresed on a 1.0% agarose gel and the DNA obtained from 800 bp was purified. The purified DNA and the pCL vector were treated with KpnI at 37° C. overnight, purified further, and the leuE gene and pCL-asd-pntAB vector were cloned. The cloned plasmids were transformed into *E. coli* DH5a, and the transformed *E. coli* DH5a was selected in LB plate medium containing spectinomycin (50 μg/mL) and the plasmids were obtained therefrom. The thus-prepared plasmids were introduced into the WCJM strain, which is a strain producing O-acetylhomoserine, and a flask evaluation was performed with regard to its productivity of O-acetylhomoserine. The thus-prepared plasmids were a total of 4 kinds and the wild-type and 3 modified strains prepared in Example 2-1 were used. The 4 kinds of plasmids were introduced into the WCJM strain by electroporation and a flask evaluation was performed in the same manner as in Example 3-1. The results are shown in Table 6-1 below.

TABLE 6

Measurement of O-acetylhomoserine production by flask culture

| | OD (562 nm) | Glucose Consumption (g/L) | O-AH (g/L) |
|---|---|---|---|
| WCJM/pCL-asd-pntAB | 9.8 | 36 | 1.8 |
| WCJM/pCL-asd-pntAB-leuE WT | 9.5 | 37 | 2.0 |
| WCJM/pCL-asd-pntAB-leuE WT_M3 | 8.2 | 38 | 3.0 |
| WCJM/pCL-asd-pntAB-leuE WT_M4 | 7.5 | 38 | 4.2 |
| WCJM/pCL-asd-pntAB-leuE WT_M6 | 7.8 | 38 | 5.9 |

As can be seen in Table 6 above, as a result of simultaneously enhancing the biosynthesis pathway and the leuE modification, the productivity of O-acetylhomoserine was further improved. In particular, in the case of the strain in which the pCL-asd-pntAB-leuE WT_M6 plasmid was introduced, the OD was decreased compared to that of the wild-type strain, but the strain showed more rapid glucose consumption and produced O-acetylhomoserine at a concentration of 5.9 g/L, the highest among the strains.

Example 4: Preparation of leuE Modification by Saturated Mutagenesis and Evaluation of Productivity of O-Acetylhomoserine 4-1. Preparation of Strains with leuE Modification by Saturated Mutagenesis and Evaluation Thereof Modifications were prepared by saturated mutagenesis to produce different types of amino acid substitutions of the 3 leuE variants, which had shown high productivity of O-acetylhomoserine. The substituted amino acids were prepared using 17 kinds of M3 mutation, M4 mutation, and M6 mutation, respectively, using the plasmids prepared in Example 2 as the templates. The details are shown in Table 7 below.

TABLE 7

| Modified Plasmid | Amino Acid Substituted | SEQ ID NO of Primers |
|---|---|---|
| M3 | L95F | SEQ ID NOS: 31, 32 |
| | L95A | SEQ ID NOS: 33, 34 |
| | L95G | SEQ ID NOS: 35, 36 |
| | L95T | SEQ ID NOS: 37, 38 |
| | L95N | SEQ ID NOS: 39, 40 |
| | L95D | SEQ ID NOS: 41, 42 |
| | L95H | SEQ ID NOS: 43, 44 |
| | L95I | SEQ ID NOS: 45, 46 |
| | L95S | SEQ ID NOS: 47, 48 |
| | L95P | SEQ ID NOS: 49, 50 |
| | L95Y | SEQ ID NOS: 51, 52 |
| | L95Q | SEQ ID NOS: 53, 54 |
| | L95K | SEQ ID NOS: 55, 56 |
| | L95E | SEQ ID NOS: 57, 58 |
| | L95C | SEQ ID NOS: 59, 60 |
| | L95W | SEQ ID NOS: 61, 62 |
| | L95R | SEQ ID NOS: 63, 64 |
| M4 | F30W | SEQ ID NOS: 65, 66 |
| | F30L | SEQ ID NOS: 67, 68 |
| | F30V | SEQ ID NOS: 69, 70 |
| | F30G | SEQ ID NOS: 71, 72 |
| | F30S | SEQ ID NOS: 73, 74 |
| | F30N | SEQ ID NOS: 75, 76 |
| | F30D | SEQ ID NOS: 77, 78 |
| | F30H | SEQ ID NOS: 79, 80 |
| | F30I | SEQ ID NOS: 81, 82 |
| | F30P | SEQ ID NOS: 83, 84 |
| | F30Y | SEQ ID NOS: 85, 86 |
| | F30Q | SEQ ID NOS: 87, 88 |
| | F30K | SEQ ID NOS: 89, 90 |
| | F30E | SEQ ID NOS: 91, 92 |
| | F30C | SEQ ID NOS: 93, 94 |
| | F30T | SEQ ID NOS: 95, 96 |
| | F30R | SEQ ID NOS: 97, 98 |
| M6 | F165W | SEQ ID NOS: 99, 100 |
| | F165L | SEQ ID NOS: 101, 102 |
| | F165V | SEQ ID NOS: 103, 104 |
| | F165G | SEQ ID NOS: 105, 106 |
| | F165S | SEQ ID NOS: 107, 108 |
| | F165N | SEQ ID NOS: 109, 110 |
| | F165D | SEQ ID NOS: 111, 112 |
| | F165H | SEQ ID NOS: 113, 114 |
| | F165I | SEQ ID NOS: 115, 116 |
| | F165P | SEQ ID NOS: 117, 118 |
| | F165Y | SEQ ID NOS: 119, 120 |
| | F165Q | SEQ ID NOS: 121, 122 |
| | F165K | SEQ ID NOS: 123, 124 |
| | F165E | SEQ ID NOS: 125, 126 |
| | F165C | SEQ ID NOS: 127, 128 |
| | F165T | SEQ ID NOS: 129, 130 |
| | F165R | SEQ ID NOS: 131, 132 |

Specifically, leuE-modified genes were prepared by performing a site-directed mutagenesis kit (Stratagene, USA) using the primers shown in Table 7 above. The plasmid was introduced into the WCJM strain and the flask was evaluated in the same manner as Example 3-1. The results are shown in Table 8 below.

TABLE 8

Measurement of O-acetylhomoserine production by flask culture

| Strain | Plasmid | Location of Modification | OD (562 nm) | Glucose Consumption (g/L) | O-AH (g/L) |
|---|---|---|---|---|---|
| WCJM | pCL1920 | | 9.6 | 35 | 1.3 |
| | pCL-leuE WT | | 8.4 | 36 | 1.5 |
| | pCL-leuE WT_M3 | L95V | 8.2 | 38 | 2.3 |
| | pCL-leuE WT_M4 | F30A | 7.9 | 38 | 3.7 |
| | pCL-leuE WT_M6 | F165A | 8.0 | 39 | 4.8 |
| | M3 Modification | L95F | 8.6 | 38 | 2.3 |
| | | L95A | 8.3 | 38 | 2.2 |
| | | L95G | 9.2 | 37 | 2.1 |
| | | L95T | 9.4 | 37.5 | 2.3 |
| | | L95N | 8.8 | 38 | 2.4 |
| | | L95D | 8.7 | 36 | 2.2 |
| | | L95H | 9.5 | 35 | 2.3 |
| | | L95I | 9.5 | 37.5 | 2.2 |
| | | L95S | 9.3 | 37 | 2.5 |
| | | L95P | 9.2 | 36 | 2.5 |
| | | L95Y | 8.9 | 35 | 2.2 |
| | | L95Q | 9.4 | 38 | 3.1 |
| | | L95K | 9.2 | 38.5 | 2.2 |
| | | L95E | 8.6 | 37 | 2.6 |

TABLE 8-continued

Measurement of O-acetylhomoserine production by flask culture

| Strain | Plasmid | Location of Modification | OD (562 nm) | Glucose Consumption (g/L) | O-AH (g/L) |
|---|---|---|---|---|---|
| | | L95C | 8.9 | 37.5 | 2.4 |
| | | L95W | 9.9 | 38 | 2.1 |
| | | L95R | 9.3 | 38 | 2.3 |
| | M4 Modification | F30W | 7.5 | 38 | 3.2 |
| | | F30L | 7.2 | 36 | 3.1 |
| | | F30V | 7.3 | 35 | 2.6 |
| | | F30G | 8.3 | 36 | 3.4 |
| | | F30S | 7.9 | 35 | 3.6 |
| | | F30N | 8.2 | 37 | 3.5 |
| | | F30D | 8.6 | 38 | 3.0 |
| | | F30H | 8.8 | 34 | 2.9 |
| | | F30I | 8.3 | 35 | 3.5 |
| | | F30P | 8.6 | 35.5 | 3.1 |
| | | F30Y | 7.9 | 34 | 2.9 |
| | | F30Q | 8.6 | 34 | 2.8 |
| | | F30K | 8.8 | 35 | 3.1 |
| | | F30E | 7.6 | 35.5 | 2.5 |
| | | F30C | 7.9 | 35 | 2.4 |
| | | F30T | 8.9 | 36 | 3.0 |
| | | F30R | 8.6 | 38.5 | 2.9 |
| | M6 Modification | F165W | 8.2 | 39 | 4.2 |
| | | F165L | 8.3 | 38 | 4.5 |
| | | F165V | 8.4 | 38 | 4.1 |
| | | F165G | 8.0 | 39 | 4.6 |
| | | F165S | 7.9 | 37 | 4.7 |
| | | F165N | 8.8 | 39 | 4.7 |
| | | F165D | 7.8 | 38 | 4.5 |
| | | F165H | 7.9 | 38 | 4.5 |
| | | F165I | 7.8 | 37 | 4.1 |
| | | F165P | 7.7 | 37.5 | 4.2 |
| | | F165Y | 8.2 | 38 | 4.6 |
| | | F165Q | 8.4 | 38 | 3.9 |
| | | F165K | 7.6 | 39 | 4.0 |
| | | F165E | 7.7 | 36.5 | 4.2 |
| | | F165C | 7.6 | 36.5 | 4.3 |
| | | F165T | 8.5 | 34 | 3.7 |
| | | F165R | 8.3 | 38 | 3.9 |

As can be seen in Table 8 above, as a result of evaluating each of the modified strains, there was a slight difference in OD and glucose consumption rate. However, all of the above modified strains were found to have an enhanced amount of O-acetylhomoserine production compared to the WCJM/pCL1920 and WCJM/pCL-leuE WT strains used as the control group.

4-2. Preparation of Strain with Enhanced leuE-Modification in Strain with High-Yield of O-Acetylhomoserine and Evaluation of its Productivity of O-Acetylhomoserine A method for producing a strain capable of producing O-acetylhomoserine by using a strain capable of producing threonine via NTG mutation derived from wild-type W3110 is disclosed (International Patent Publication No. WO 2012/087039). In particular, the thus-prepared strain producing O-acetylhomoserine with high yield was deposited with the Korean Microorganism Conservation Center under the Accession No. KCCM11146P.

An attempt was made whether the productivity of O-acetylhomoserine can be further enhanced by introducing the leuE gene and modified strains thereof based on the above strain.

Specifically, the leuE gene and 3 modified strains thereof were introduced by electroporation. The strains introduced were named as KCCM11146P/pCL1920, KCCM11146P/pCL-leuE WT, KCCM11146P/pCL-leuE M3, KCCM11146P/pCL-leuE M4, and KCCM11146P/pCL-leuE M6, respectively. To measure the productivity of O-acetylhomoserine of the leuE gene and 3 modified strains thereof, flask culture evaluation was performed. Specifically, LB medium was inoculated with 4 kinds of the above strains and incubated overnight at 33° C. Then, single colonies were inoculated into 3 mL of LB medium and cultured again at 33° C. for 5 hours, diluted 200-fold in a 250 mL Erlenmeyer flask containing 25 mL of medium for producing O-acetylhomoserine, and incubated again at 33° C. at 200 rpm for 30 hours, and the amount of O-acetylhomoserine production was confirmed by HPLC analysis. The results of the experiment are summarized in Table 9 below.

TABLE 9

Measurement of O-acetylhomoserine production by flask culture

| | OD (562 nm) | Glucose Consumption (g/L) | O-AH (g/L) |
|---|---|---|---|
| KCCM11146P/pCL1920 | 18.3 | 40 | 14.2 |
| KCCM11146P/pCL-leuE WT | 17.9 | 40 | 16.3 |
| KCCM11146P/pCL-leuE M3 | 17.5 | 40 | 16.9 |
| KCCM11146P/pCL-leuE M4 | 16.8 | 40 | 19.2 |
| KCCM11146P/pCL-leuE M6 | 17.2 | 40 | 18.8 |

As can be seen in Table 9 above, it was confirmed that the strain which was prepared by introducing only the pCL1920 into the KCCM11146P strain produced 14.2 g/L of O-acetylhomoserine, and the leuE WT strain also showed an increase in the amount of O-acetylhomoserine production compared to the original strain. Additionally, all of the 3 modified strains showed a decrease of OD, whereas the M4 strain showed the highest yield of O-acetylhomoserine production (19.2 g/L). The M4 and M6 strains showed an increase in the amount of the O-acetylhomoserine production.

The inventors of the present disclosure confirmed that the O-acetylhomoserine production was increased in "KCCM11146P/pCL-leuE M3, M4, and M6 strains", which are 3 leuE-modified strains of M3, M4, and M6 based on the KCCM11146P strain. As a result, they named the strains as "CA05-4009", "CA05-4010", and "CA05-4011", and were deposited with the KCCM on Dec. 15, 2014, under the Accession Nos. KCCM11645P, KCCM11646P, and KCCM11647P, respectively.

Example 5: Production of L-Methionine Using O-Acetylhomoserine Culture Solution Produced and Transferase An experiment for producing L-methionine by using the culture solution of O-acetylhomoserine obtained in Example 4 and O-acetylhomoserine sulfhydrylase, which is an enzyme converting O-acetylhomoserine to methionine, was performed.

O-Acetylhomoserine sulfhydrylase, a converting enzyme, was prepared by the method provided in Example 1-2 of Korean Patent No. 10-1250651, and the amount of L-methionine produced by a conversion reaction using the method provided in Example 3 of Korean Patent No. 10-1250651 was measured. For the O-acetylhomoserine used as the substrate, the culture solution of KCCM11146P-pCL-leuE M4 (O-AH concentration; 19.2 g/L) obtained in Example 4 in the present disclosure was used, and the concentration of the L-methionine produced therefrom is shown in Table 10 below.

TABLE 10

| | | Time (min) | | | | |
|---|---|---|---|---|---|---|
| | | 2 | 4 | 6 | 8 | 10 |
| MetZ-rsp | Methionine (g/L) | 3.21 | 4.34 | 4.52 | 4.78 | 5.04 |
| | Conversion (%) | 50% | 68% | 71% | 75% | 79% |

As can be seen in Table 10 above, it was confirmed that the O-acetylhomoserine contained in the culture solution of the KCCM11146P-pCL-leuE M4 strain obtained in Example 4 was converted to methionine at a conversion rate of 79% for 10 minutes. From this result, it was confirmed that methionine can be successfully produced using the strain of the present disclosure.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A polynucleotide encoding a polypeptide having the activity of exporting O-acetylhomoserine, wherein at least one amino acid selected from the group consisting of phenylalanine at position 30, leucine at position 95, and phenylalanine at position 165 in the amino acid sequence of SEQ ID NO: 1 is substituted with another amino acid.

2. The polynucleotide according to claim 1, wherein the polynucleotide is selected from the group consisting of nucleic acid sequences of SEQ ID NOS: 135, 136, 139, 140, 143, and 144.

3. A microorganism of the genus *Escherichia* producing O-acetylhomoserine, wherein a polypeptide consisting of the amino acid sequence of SEQ ID NO: 1 or a modified polypeptide thereof is comprised or overexpressed, wherein, with regard to the modified polypeptide, at least one amino acid selected from the group consisting of phenylalanine at position 30, leucine at position 95, and phenylalanine at position 165 in the amino acid sequence of SEQ ID NO: 1 is substituted with another amino acid.

4. The microorganism according to claim 3, wherein, with regard to the modified polypeptide, phenylalanine at position 30 in the amino acid sequence of SEQ ID NO: 1 is substituted with any one selected from the group consisting of alanine, tryptophan, leucine, valine, glycine, serine, asparagine, aspartic acid, and histidine; leucine at position 95 in the amino acid sequence of SEQ ID NO: 1 is substituted with any one selected from the group consisting of valine, phenylalanine, alanine, glycine, threonine, asparagine, aspartic acid, and histidine; or phenylalanine at position 165 in the amino acid sequence of SEQ ID NO: 1 is substituted with any one selected from the group consisting of alanine, tryptophan, leucine, valine, glycine, serine, asparagine, aspartic acid, and histidine.

5. The microorganism according to claim 3, wherein, with regard to the modified polypeptide, valine at position 1 in the amino acid sequence of SEQ ID NO: 1 is further substituted with methionine.

6. The microorganism according to claim 3, wherein the microorganism of the genus *Escherichia* is *Escherichia coli*.

7. The microorganism according to claim 3, wherein, additionally, the activity of cystathionine synthase is inactivated.

8. The microorganism according to claim 3, wherein, additionally, the activity of homoserine kinase is inactivated.

9. The microorganism according to claim 3, wherein, additionally, the activity of homoserine acetyltransferase is enhanced compared to that of an unmodified microorganism.

10. The microorganism according to claim 3, wherein, additionally, the activities of aspartate semialdehyde dehydrogenase, pyridine nucleotide transhydrogenase, or a combination thereof is enhanced compared to that of an unmodified microorganism.

11. A method for producing O-acetylhomoserine, comprising:
culturing the microorganism of the genus *Escherichia* producing O-acetylhomoserine of claim 3 in a medium; and
recovering O-acetylhomoserine from the cultured microorganism or the cultured medium.

12. A method for producing L-methionine, comprising:
culturing the microorganism of the genus *Escherichia* producing O-acetylhomoserine of claim 3 in a medium; and
converting the O-acetylhomoserine to L-methionine by treating the cultured microorganism or the cultured medium or the O-acetylhomoserine recovered from the cultured microorganism or the cultured medium with methyl mercaptan and a methionine-converting enzyme.

13. The method according to claim 12, wherein the methionine-converting enzyme is O-acetylhomoserine sulfhydrylase.

* * * * *